US012788465B2

(12) United States Patent
Atkins, Jr. et al.

(10) Patent No.: US 12,788,465 B2
(45) Date of Patent: Nov. 10, 2026

(54) PULSED FIELD ELECTROPORATION SYSTEMS AND METHODS

(71) Applicant: Aventix Medical Inc., Irvine, CA (US)

(72) Inventors: James H. Atkins, Jr., San Antonio, TX (US); John Ross Saunders, Edinburgh (GB); Jetmir Palushi, Irvine, CA (US)

(73) Assignee: Aventix Medical Inc., Laguna Hills, CA (US)

( * ) Notice: Subject to any disclaimer, the term of this patent is extended or adjusted under 35 U.S.C. 154(b) by 211 days.

(21) Appl. No.: 18/613,827

(22) Filed: Mar. 22, 2024

(65) Prior Publication Data

US 2024/0390052 A1 Nov. 28, 2024

Related U.S. Application Data

(60) Provisional application No. 63/536,339, filed on Sep. 1, 2023, provisional application No. 63/504,510, filed on May 26, 2023.

(51) Int. Cl.
*A61B 18/00* (2006.01)

(52) U.S. Cl.
CPC .... *A61B 18/00* (2013.01); *A61B 2018/00077* (2013.01); *A61B 2018/00327* (2013.01); *A61B 2018/00613* (2013.01); *A61B 2018/00708* (2013.01); *A61B 2018/00714* (2013.01); *A61B 2018/00732* (2013.01); *A61B 2018/0075* (2013.01); *A61B 2018/00761* (2013.01); *A61B 2018/00767* (2013.01); *A61B 2018/00982* (2013.01)

(58) Field of Classification Search
CPC ...... A61B 18/1492; A61B 2018/00613; A61B 2018/00327; A61N 1/327
See application file for complete search history.

(56) References Cited

U.S. PATENT DOCUMENTS

| | | | | |
|---|---|---|---|---|
| 5,327,905 | A * | 7/1994 | Avitall | A61B 18/1492 606/45 |
| 8,936,594 | B2 | 1/2015 | Wolf et al. | |
| 9,072,597 | B2 | 7/2015 | Wolf et al. | |
| 9,101,384 | B2 | 8/2015 | Makower et al. | |
| 9,415,194 | B2 | 8/2016 | Wolf et al. | |
| 9,943,361 | B2 | 4/2018 | Wolf et al. | |
| 10,252,050 | B2 | 4/2019 | Kreis et al. | |
| 10,456,185 | B2 | 10/2019 | Wolf et al. | |
| 10,610,675 | B2 | 4/2020 | Deem et al. | |
| 10,722,282 | B2 | 7/2020 | Wolf et al. | |
| 10,864,035 | B2 | 12/2020 | Hester et al. | |
| 10,894,011 | B2 | 1/2021 | Deem et al. | |

(Continued)

FOREIGN PATENT DOCUMENTS

WO WO 2022/264147 A2 12/2022

OTHER PUBLICATIONS

International Search Report and Written Opinion in International Appln. No. PCT/US2024/025708, mailed on Sep. 30, 2024, 26 pages.

(Continued)

*Primary Examiner* — Sean W Collins
(74) *Attorney, Agent, or Firm* — Fish & Richardson P.C.

(57) ABSTRACT

An improved system described herein equipped with one or more Pulsed Field Electroporation (PFE) electrodes configured to cause localized and targeted PFE output at the targeted tissue, for example, in an ear, nose, or throat.

23 Claims, 20 Drawing Sheets

(56) References Cited

U.S. PATENT DOCUMENTS

| | | | |
|---|---|---|---|
| 11,033,318 B2 | 6/2021 | Wolf et al. | |
| 11,167,125 B2 | 11/2021 | Moss et al. | |
| 11,241,271 B2 | 2/2022 | Wolf et al. | |
| 11,304,746 B2 | 4/2022 | Wolf et al. | |
| 11,311,721 B2 | 4/2022 | Ebbers et al. | |
| 11,324,543 B2 | 5/2022 | Waldstreicher et al. | |
| 11,419,671 B2 | 8/2022 | Townley et al. | |
| 11,547,473 B2 | 1/2023 | Townley et al. | |
| 11,576,719 B2 | 2/2023 | Townley et al. | |
| 11,666,378 B2 | 6/2023 | Townley et al. | |
| 11,679,077 B2 | 6/2023 | Deem et al. | |
| 11,766,286 B2 | 9/2023 | Wolf et al. | |
| 11,833,350 B2 | 12/2023 | Viswanathan et al. | |
| 11,883,091 B2 | 1/2024 | Townley | |
| 12,042,202 B1 | 7/2024 | Atkins et al. | |
| 12,082,863 B1 | 9/2024 | Atkins et al. | |
| 12,484,946 B2 | 12/2025 | Atkins et al. | |
| 2006/0041277 A1* | 2/2006 | Deem | A61N 1/36117 607/3 |
| 2011/0160514 A1 | 6/2011 | Long et al. | |
| 2012/0109122 A1* | 5/2012 | Arena | A61N 1/327 606/41 |
| 2018/0103994 A1* | 4/2018 | Fox | A61B 5/4893 |
| 2019/0247680 A1* | 8/2019 | Mayer | A61B 17/32 |
| 2020/0046955 A1 | 2/2020 | Deem et al. | |
| 2020/0261149 A1 | 8/2020 | Shameli et al. | |
| 2021/0236816 A1 | 8/2021 | Waldstreicher et al. | |
| 2022/0087739 A1 | 3/2022 | Paulushi et al. | |
| 2022/0313353 A1 | 10/2022 | Paulushi et al. | |
| 2023/0054079 A1 | 2/2023 | Lakshmi | |
| 2024/0277393 A1* | 8/2024 | Beyar | A61B 18/1485 |
| 2024/0392286 A1 | 11/2024 | Atkins et al. | |

OTHER PUBLICATIONS

K. N. Aycock, Y. Zhao, M. F. Lorenzo and R. V. Davalos, “A Theoretical Argument for Extended Interpulse Delays in Therapeutic High-Frequency Irreversible Electroporation Treatments,” in IEEE Transactions on Biomedical Engineering, vol. 68, No. 6, pp. 1999-2010, Jun. 2021 (Year: 2021).

International Preliminary Report on Patentability in International Appln. No. PCT/US2024/025708, mailed on Dec. 11, 2025, 15 pages.

Extended European Search Report in European Appln. No. 24816086.3, mailed on Jul. 15, 2026, 7 pages.

* cited by examiner

PULSED FIELD ELECTROPORATION SYSTEMS AND METHODS

This application claims the benefit of U.S. Provisional Patent Application Nos. 63/504,510 (filed on May 26, 2023) and 63/536,339 (filed on Sep. 1, 2023). The entire content of each of these applications is incorporated herein by reference.

TECHNICAL FIELD

This disclosure pertains to Pulsed Field Electroporation (PFE), such as PFE systems for use in Ear, Nose, and Throat (ENT) procedures.

BACKGROUND

PFE is a kind of electrical stimulation therapy that involves delivering short, high-amplitude electrical pulses to targeted tissue of a patient. These electrical pulses create temporary pores in the cell membranes of affected cells, causing permeabilization of the membrane without significant damage to the cells. PFE can be used to treat unwanted or diseased tissue, for example, by triggering healthy and natural tissue regeneration where the stimulus is applied.

Chronic rhinitis is a condition characterized by inflammation of the nasal mucosa, leading to persistent symptoms such as nasal congestion, runny nose, sneezing, and nasal itching. It can be caused by various factors, including allergies, infections, irritants, or structural abnormalities in the nose. Chronic rhinitis can affect several parts of the body, primarily the nasal cavity and adjacent structures. Inflammation of the nasal mucosa can lead to swelling and congestion of the nasal passages, resulting in difficulty breathing through the nose. Chronic rhinitis can extend to the paranasal sinuses, which are air-filled cavities located around the nasal cavity.

When treating chronic rhinitis conditions or other tissue in the nasal cavity, practitioners can assess factors such as time, patient comfort, risk of injury to healthy tissue and adjacent structures. The length of time required to do such procedures in the nasal cavity may vary significantly, especially for those circumstances where the procedure includes the delivery of thermal ablative energy, such as from Radiofrequency (RF), Cryoablation (CA), or lasers, for purposes of treating nasal conditions. PFE therapy is different from these thermal ablative procedures at least because each of RF, CA, and lasers use thermal energy to intentionally induce cell death by a process called "necrosis." In doing so, the use of these thermal ablative techniques may generate significant temperature change (significantly higher or lower than the normal body temperature, such as a tissue temperature increase of 10-degrees C. or more) at the targeted tissue area, which causes inflammatory effects (and often painful crust formation) along the ablated tissue. In doing so, these thermal ablative techniques can also increase the risk of unintended injury to healthy tissue in certain cases. For example, if RF ablation energy is delivered in a targeted tissue area, and soon thereafter more thermal energy is delivered in such a way that the first lesion and the second lesion are overlapped, the overlapped region of ablation may be at higher risk of severe crusting or scab formation when compared to a non-overlapping lesion. Also, these thermal ablation instruments (e.g., RF, CA, and lasers) may cause complications during nasal procedures where the thermal profile may extend their ablative effects beyond the targeted tissue type and into other types of tissues and adjacent structures. For example, during such necrosis-inducing energy delivery, extension of the zone of ablative effects past the targeted tissue may lead to unintended damage of critical structures such as arteries and nerves that are proximate to the active electrode or are exposed to the elevated temperatures for long periods of time.

SUMMARY

Some embodiments described herein can include an improved system that is configured to access, engage, and controllably deliver pulsed field electroporation (PFE) to a targeted tissue within an ear, nose, or throat, such as a targeted location at the postnasal nerve region, the inferior turbinate region, the retropalatal region, the retroglossal region, the hypopharyngeal region, the sphenopalatine ganglion tissue region, the Eustachian tube, the nasal cavity, the paranasal sinuses, the trigeminal nerve region, the tonsils, or the adenoids region. In particular implementations, the PFE can induce electroporation in the targeted tissue and stimulate one or more nerves proximate to the target tissue. As described in additional detail below, some embodiments of the system can cause localized PFE by using an electric field, which is applied to the targeted tissue in rapid bursts to cause irreversible electroporation (IRE). This induces cell membrane destabilization to cause a particular type of cell death called "apoptosis." As such, these embodiments of the PFE instruments can treat the targeted tissue to cause apoptosis, a cell death process that is similar to a natural and controlled part of anatomical growth or development, while avoiding the thermal ablation energy (e.g., from RF, CA, or laser ablation) that induces the above-described necrosis. Optionally, the PFE system described herein can be configured to output PFE energy in a manner that selectively targets the predetermined tissue type to be treated, which can thereby reduce cell inflammation and avoid complications associated with traditional thermal ablation energy (from RF, CA, and lasers) with ablative effects extended outside of the targeted treatment zone.

According to some embodiments described herein, an improved PFE system may integrate PFE to more effectively treat the targeted tissue while reducing the likelihood of injuring the non-targeted tissue (as may occur with the necrosis-inducing ablation instruments, such as RF ablation, CA ablation, or laser ablation systems). For example, the improved system described herein can be configured to output PFE to selectively and non-thermally open the cell pores in the targeted tissue to induce apoptosis which may reduce the likelihood of damaging non-targeted tissue such as blood vessels, nerves, and others. In many cases, the improved system can accomplish such treatment without the use of general anesthesia on the patient, thereby providing added convenience for both the user and the patient. For example, the improved system can accomplish such treatment using a topical anesthetic at the treatment site. Optionally, some versions of the improved system with integrated PFE may also be used to more efficiently deliver drugs, such as steroids, to the targeted tissue as compared with systems that treat tissue without PFE. A method of tracking the treated anatomical space and correlating the treatment spaces to outcomes is also disclosed.

In some options described herein, the system can be configured to deliver PFE for one or both of two distinct effects to the targeted tissue. The first type, as described above, is related to irreversible electroporation (IRE) which triggers cell death by the above-described process of apoptosis, and the second type is reversible electroporation (RE)

where the cell membrane pores are enlarged so that large molecule drugs, such as steroids, can permeate through the cell membrane without inducing apoptosis. Both of irreversible electroporation and reversible electroporation can be non-thermal, meaning that these kinds of electroporation therapy do not deliver thermal ablative energy (e.g., heat from an RF ablation instrument) that kills cells via necrosis.

In various embodiments described below, the waveform of the PFE system can be controlled to also stimulate the nerves located in proximity to the electroporation electrode of the PFE device. For example, electrical pulses can cause action potentials to propagate through nerves of a patient, and thus stimulate neural activity. In some examples, a neurostimulation effect of PFE is desired so it resets the nerve activity, thus resulting in normal nerve signaling communication of the nerve. Optionally, this method of PFE can add benefits in such a way that the nerve activity may be modulated to potentially reduce neuralgia.

In some embodiments, a PFE device can deliver PFE that has at least two different frequency components. For example, the PFE can include a sequence of bursts of electrical pulses occurring at a first frequency. Each of these bursts can include a high-frequency pulse train at a second frequency that is significantly higher than the first frequency. The high frequency bursts can induce irreversible electroporation leading to the above-described apoptosis. The gaps between high frequency bursts allow for neurostimulation of nerves proximate to the targeted tissue. This is because action potentials that are evoked by electrical stimulation of first frequency while the second frequency (high frequency) may not evoke stimulation to the nerves. The gaps between individual pulses of a burst can be too small to allow for stimulation in this way.

In optional embodiments detailed below, a machine learning model can be implemented with the PFE system so as to determine a PFE treatment dosage based on a particular procedure being performed and a detected type of tissue proximate an instrument for delivering PFE. For example, a machine learning model can receive endoscope data indicating a location of the instrument relative to one or more anatomical features (e.g., kinds of tissue). The machine learning model can determine a PFE dosage based on the endoscope data independently without user input. Additionally, or alternatively, the machine learning algorithm can enable PFE activation, readjust one or more PFE pulse parameters (e.g., frequency, amplitude), activate neurostimulation effects when certain anatomy is detected in the endoscope data, or any combination thereof. In one embodiment, the machine learning model can cause a PFE instrument configured for treating the inferior turbinate to deliver PFE pulses when endoscope data indicates that a PFE electrode is within the inferior turbinate region. By using a machine learning model to determine therapy based on endoscope data, the system can improve PFE treatment delivery as compared with systems that do not use a machine learning model to determine therapy.

Some embodiments described herein include a system that comprises a PFE delivery instrument. The PFE delivery instrument may include a handle, an elongated shaft extending distally from the handle, and a treatment tip (having a PFE electrode) at a distal end portion of the elongated shaft. Optionally, the treatment tip may have an expandable PFE electrode for securing the PFE instrument in place such that the treatment tip is configured to deliver PFE from the PFE electrode at nasal tissue.

Some embodiments described herein include a method for delivering PFE therapy. The method can include inserting an elongated shaft of a PFE delivery instrument into an ear, nose, or throat site such that a PFE electrode of a treatment tip at a distal end of the PFE delivery instrument is adjacent to a targeted tissue. The method may optionally include adjusting the PFE electrode relative to the elongated shaft. Additionally, the method may include activating a PFE generator of a control console connected to the PFE delivery instrument to output an electric field in a predefined pattern from the PFE electrode to induce at least one of irreversible electroporation (IRE) at the targeted tissue and reversible electroporation (RE) at the targeted tissue.

A number of embodiments herein include a system that comprises a pulsed field electroporation (PFE) generator configured to output pulsed PFE energy. The system may also include a touchscreen interface coupled to the generator configured to receive user input to control PFE characteristics output from the generator. In some embodiments, the touchscreen interface can be connected to an endoscope system so that the touchscreen interface can display endoscope imaging data in real time. This imaging data can indicate the location of the PFE instrument relative to one or more anatomical features. Optionally, the system can include a PFE delivery instrument including an elongated shaft and a PFE electrode to deliver the PFE energy from the PFE generator to at least one of a the postnasal nerve region, the inferior turbinate region, the retropalatal region, the retroglossal region, the hypopharyngeal region, the sphenopalatine ganglion tissue region, the Eustachian tube, the nasal cavity, the paranasal sinuses, the trigeminal nerve region, the tonsils, the adenoids region, and other ear, nose, and throat sites.

Further embodiments described herein include a method of using a PFE instrument. The method can include advancing a treatment tip of a PFE instrument into a subject such that a PFE electrode along the treatment tip is proximate to a targeted site. Optionally, the method can include outputting a PFE waveform from the PFE electrode of the treatment tip to induce apoptosis at the targeted site and/or stimulate nerves proximate to the targeted site.

Additional embodiments described herein include a PFE method of treating targeted tissue of an ear nose, or throat—preferably, without application of general anesthesia. The method can include compressing a PFE electrode against the targeted tissue while outputting a PFE waveform from the PFE electrode.

Some embodiments described herein include a method of delivering a pulsed waveform to targeted tissue of an ear nose, or throat—preferably, without increasing the temperature of the targeted tissue more than 5-degree C. and thus safely avoiding the above-described necrosis of thermal ablation techniques. The method can include advancing a treatment tip of a PFE instrument such that a PFE electrode along the treatment tip is proximate to targeted tissue of an ear nose, or throat. Optionally, the method can include outputting a PFE energy waveform from the PFE electrode of the treatment tip to induce apoptosis at the targeted tissue. Because the PFE energy wave form can include pulses for non-thermal treatment-again, with little or no temperature change at the targeted tissue (preferably a change of 0 to 5-degrees C.) to thereby avoid the above-described necrosis of thermal ablation techniques and the accompanying side effects—the PFE instrument can treat the targeted tissue via apoptosis triggering healthy and natural tissue regeneration at the treatment site.

Some implementations described herein include a PFE system configured to deliver PFE pulses to nasal tissue. The PFE system can include a handheld PFE tool and a PFE control console. The a handheld PFE tool can optionally include a handle, an elongated shaft extending distally from the handle toward a bendable distal shaft portion, and a bulbous treatment tip extending distally from the bendable distal shaft portion. The bulbous treatment tip may include a PFE electrode configured to deliver PFE pulses to nasal tissue adjacent to the bulbous treatment tip, and the bulbous treatment tip can have a maximum lateral width of less than 5 mm and may be insertable into a nasal passageway. Optionally, the PFE control console can be configured to receive a connector of the handheld PFE tool and may include a user interface display and a PFE generator. The PFE generator of the PFE control console may optionally be configured to output from the PFE electrode a pulsed field according to a predefined pattern of pulses having a voltage within a range from 850 V to 10,000 V and a pulse duration of 0.05 microseconds (μs) to 3 μs to induce irreversible electroporation in the nasal tissue.

Particular implementations described herein include a PFE system including an electrical stimulation tool. The electrical stimulation tool can include a handle, an elongated shaft extending distally from the handle, and one or more electrodes at a distal end portion of the elongated shaft. Optionally, the electrical stimulation tool of the PFE system is configured to deliver electrical stimulation therapy to nasal tissue of a patient via the one or more electrodes, and the electrical stimulation therapy can both induce electroporation in the nasal tissue and stimulate one or more nerves proximate to the one or more electrodes.

Further implementations described herein include a PFE system comprising an electrical stimulation tool and an endoscope. The electrical stimulation tool can include a handle, an elongated shaft extending distally from the handle, and one or more electrodes at a distal end portion of the elongated shaft insertable into a nasal passageway. Preferably, the electrical stimulation tool is configured to induce electroporation in nasal tissue via the one or more electrodes while the endoscope is configured to capture the distal end portion within the nasal passageway of the patient.

Some implementations described herein include a method of providing PFE therapy in an ear, nose, or throat. The method may include inserting an elongated shaft of a handheld PFE tool into the ear, nose, or throat such that one or more electrodes located at a distal end portion of the elongated shaft are adjacent to targeted tissue. Optionally, the method may include delivery of PFE pulses from the one or more electrodes of the handheld PFE tool subsequent to a computer-controlled determination to activate electrical stimulation therapy to the targeted tissue.

Particular implementations described herein include a PFE system having a generator configured to deliver PFE therapy via an electrical stimulation tool to induce irreversible electroporation at targeted tissue. The PFE system can optionally include a PFE console including at least one machine learning algorithm executable by a processor of the PFE console to detect anatomical regions, determine whether to enable or disable PFE therapy delivery, to overlay a graphic of a PFE field proximate to a medical image of the electrical stimulation tool, or a combination thereof.

Implementations described herein can include any or all of the following features. Other features, aspects and potential advantages will be apparent from the accompanying description and figures.

DETAILED DESCRIPTION

Figure 1:
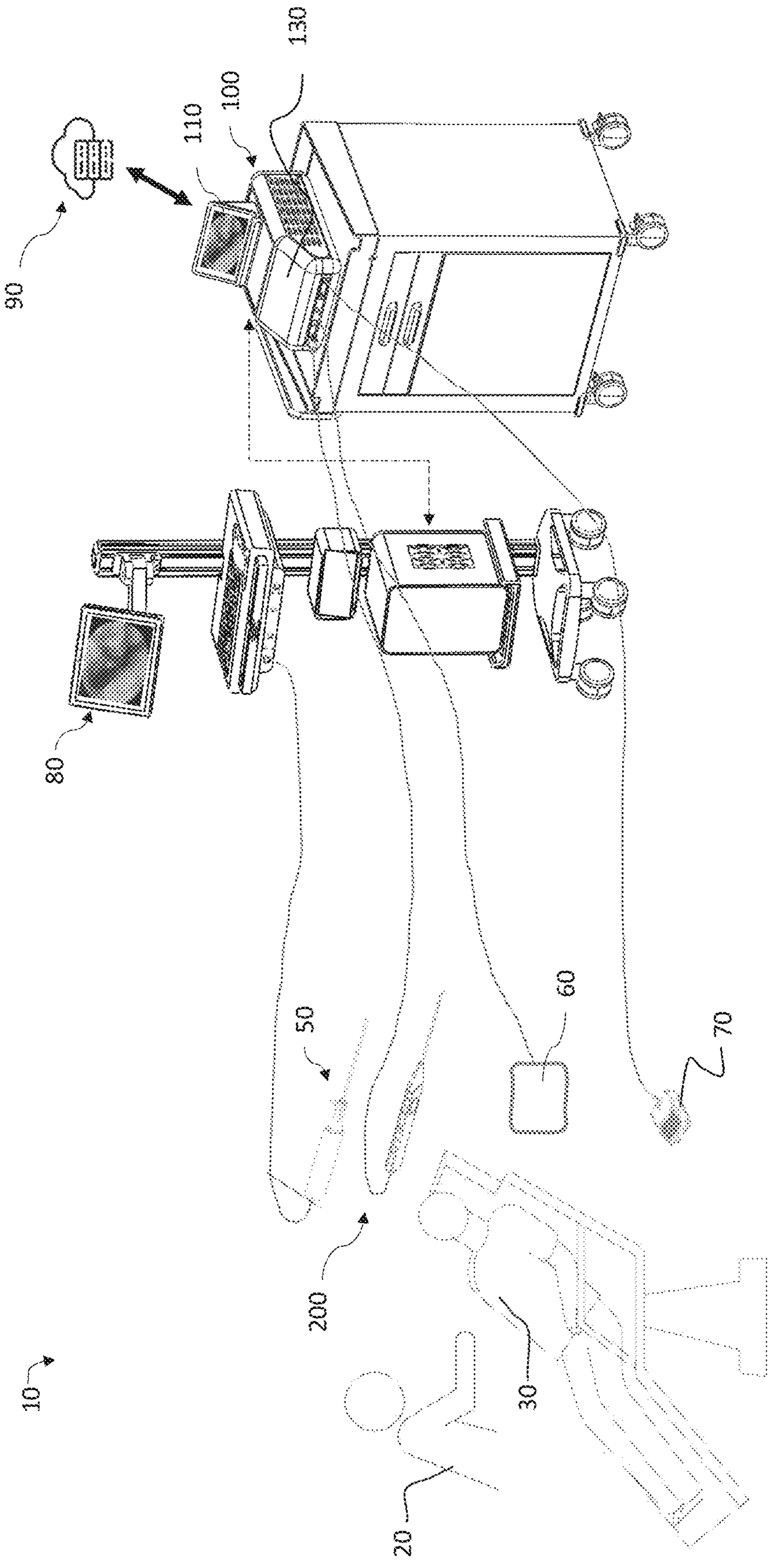
FIG. 1 shows a perspective view of a system for treating ear, nose, or throat tissue, in accordance with some embodiments.
Figure 2:
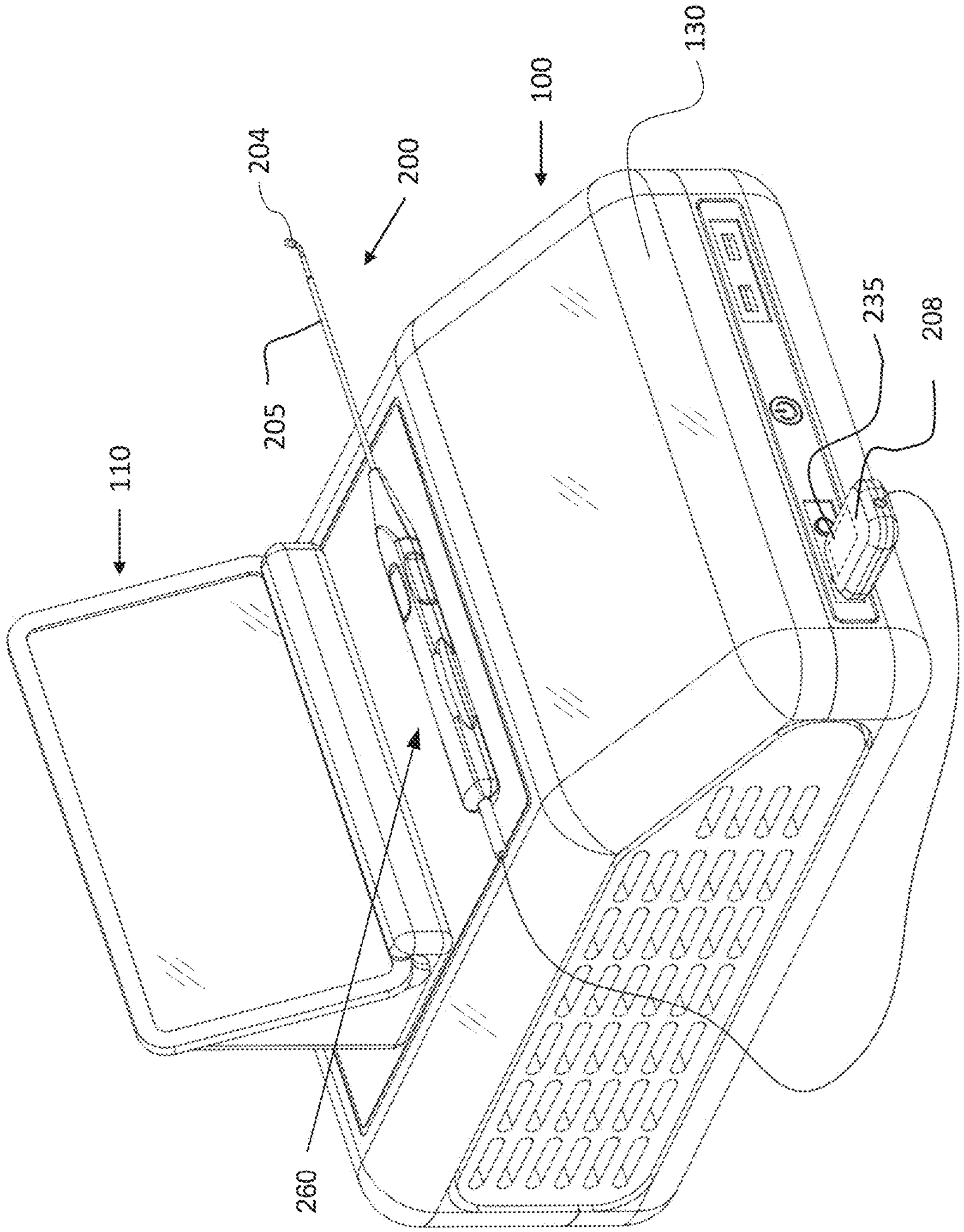
FIG. 2 shows a perspective view of a PFE console, user interface and instrument of the system of FIG. 1, in accordance with some embodiments.
Figure 3:
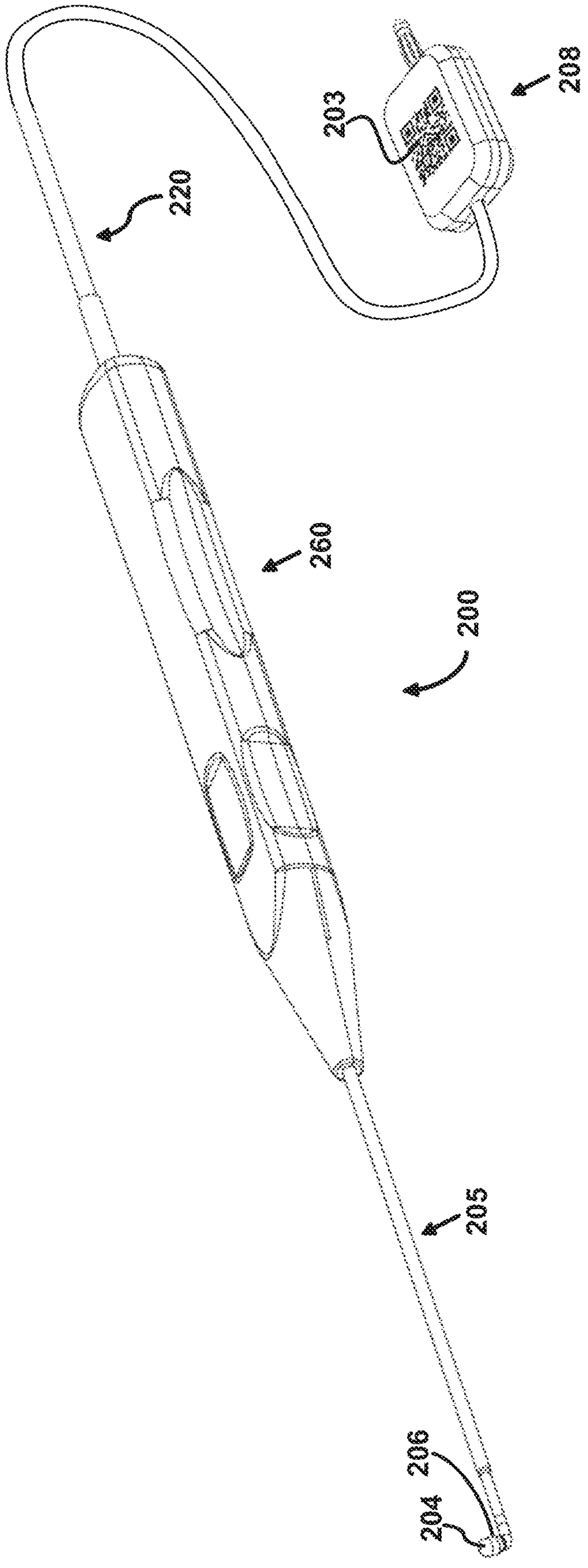
FIG. 3 is perspective view of the instrument of FIG. 2, in accordance with some embodiments.

Referring now to FIGS. 1-3, some embodiments of a system 10 for treating ear, nose, or throat tissue can include a Pulsed Field Electroporation (PFE) control console 100 and a PFE delivery instrument 200. PFE delivery instrument 200 can be configured to access and engage a targeted tissue at any of the postnasal nerve region, the inferior turbinate region, the retropalatal region, the retroglossal region, the hypopharyngeal region, the sphenopalatine ganglion tissue region, the Eustachian tube, the nasal cavity, the paranasal sinuses, the trigeminal nerve region, the tonsils, the adenoids region, and other ear, nose, and throat sites while contemporaneously delivering PFE to the targeted tissue. For example, a user 20 can guide the instrument 200 into a nose of a patient 30 and activate the PFE control console 100 so that PFE delivery instrument 200 can deliver PFE to treat swollen or diseased tissue. The PFE therapy controlled by the treatment waveform from the PFE control console 100 can induce apoptosis in the cells of the swollen or diseased tissue, thereby triggering healthy and natural tissue regeneration at the treatment site. Control console 100 includes a generator 130 configured to output a PFE signal via PFE delivery instrument 200. Control console 100 also includes a user interface device 110. The PFE delivery instrument 200 can be removably attachable to the control console 100 such that control console 100 is configured to connect with multiple instruments 200 over time. This means that control console 100 can store and/or transmit information concerning these multiple instruments, as described in further detail below.

PFE delivery instrument 200 includes a distal tip 204 positioned along a distal end portion or an elongated shaft 205 ending and configured to output PFE via a one or more electrodes (such as mesh electrodes or needle-like electrodes, as detailed below). Optionally, the distal tip 204 can be equipped with an expandable member such as an expandable stent, as described in particular embodiments below. In use, the distal tip 204 of the PFE instrument is inserted into an anatomic passageway so that the PFE electrode(s) as engaged against a targeted tissue of the sinus ostia, the postnasal nerve region, the inferior turbinate region, the retropalatal region, the retroglossal region, the hypopharyngeal region, the sphenopalatine ganglion tissue region, the Eustachian tube, the nasal cavity, the paranasal sinuses, the trigeminal nerve region, the tonsils, the adenoids region, and other ear, nose, and throat sites. As described in more detail below, the system 10 can further include a footswitch 70 (for selective activation by the user 20 to initiate the output of PFE pulses from the instrument 200), a disposable ground electrode pad 60 (for temporary adhesion to the patient 30), an endoscope system 80 (for medical imaging during delivery and use of the instrument 200), and a cloud server 90 (for remote communication with the control console 100). PFE delivery instrument can include a handle 260. The elongated shaft 205 can extend distally from a distal end of the handle.

In use, PFE delivery instrument 200 is advanced to the diseased tissue which may need to be treated. In some examples, an expandable member of distal tip 204 expands at the targeted tissue to secure distal tip 204 at the targeted tissue and/or to dilate the targeted tissue. Next, control console 210 can activate the PFE electrode 206 (FIG. 3) to deliver PFE to treat targeted tissue via electroporation. Control console 100 (FIG. 1) can control one or more aspects of the delivered PFE to achieve a predetermined electric field applied to the targeted tissue in a rapid pattern that induces cell membrane destabilization at the targeted tissue and/or stimulates one or more nerves at the targeted tissue or proximate the targeted tissue. Optionally, the PFE electrode 206 may work in conjunction with the grounding electrode 60, which in the embodiment depicted in FIG. 1, is a grounding pad adhesively mounted to the patient's body.

The PFE delivered by PFE delivery instrument 200 can be configured to both induce electroporation (e.g., irreversible electroporation and/or reversible electroporation) in targeted tissue and stimulate one or more nerves in targeted tissue or proximate targeted tissue. For example, biofilms can cause chronic rhinosinusitis, and disrupting the biofilm can treat chronic rhinosinusitis. PFE can disrupt the biofilm by inducing irreversible electroporation, thus destroying the biofilm through apoptosis. Accordingly, in this embodiment, the PFE control console 100 and PFE delivery instrument can work in conjunction to controllably induce apoptosis to disrupt the biofilm and thereby treat chronic rhinosinusitis in a way that is less invasive and painful as compared with other treatments such as surgically removing the biofilm or thermally ablating the biofilm.

In some embodiments, electrical stimulation from the PFE control console 100 that induces electroporation can include pulses that have high frequency (e.g., within a range from 500 kilohertz (kHz) to 10,000 kHz) and high voltage (e.g., within a range from 850 Volts (V) to 10,000 V). Although sustained delivery of high voltage pulses at a high frequency can induce electroporation, this sustained delivery sometimes may not cause adequate neurostimulation when there are no breaks in stimulation for neural activity to take effect. In some embodiments, PFE delivery instrument 200 can deliver a sequence of high frequency bursts of high voltage pulses, with separation between the bursts during which no stimulation is delivered. This means that the high frequency bursts can induce electroporation and neural activity can take effect during the separation periods.

Thus, depending upon the waveform output from the PFE control console 100, the system 10 including PFE delivery instrument 200 can, in particular embodiments, achieve an improved system for delivering PFE that both induces electroporation and stimulates nerves. As such, the system 10 can both treat targeted tissue by treating diseased cells and/or causing apoptosis at the diseased cells while also using neurostimulation to reset nerve activity to a standard/natural activity level for that particular region of the targeted tissue.

In some embodiments, PFE delivery instrument 200 can be advanced to the targeted anatomical space under medical imaging, for example using the endoscope system 80 (FIG. 1) including a handheld endoscope instrument 50 configured to be handled by the user simultaneously with the use of the PFE delivery instrument 200. In some embodiments, The PFE generator 130 of the control console 100 can be activated by pressing a user interface button of the instrument 200 (FIG. 3), or optionally, using the footswitch 70 (FIG. 1). As detailed below, in some embodiments, the control console 100 can selectively enable the PFE output from the generator 130 in response to an authorized instrument being connected therewith, for example, by capturing an identifier 235 (e.g., QR code 203) at a connector 208 of the PFE delivery instrument 200. The control console 100 may communicate (e.g., via a wired or wireless connection to the internet) with the cloud server 90 to validate the identifier 235 of the instrument, as well as transmit treatment data from the control console 100 to the cloud server indicative of the use of that particular instrument (having the identifier 235) with the particular patient 30 on that date.

In some examples, control console 100 and/or cloud server 90 is configured to store a machine learning model. This machine learning model can be trained to perform one or more actions for controlling PFE based on input data. In some embodiments, the input data can include endoscope data (medical image data) collected by endoscope system

80. For example, endoscope instrument 50 can collect endoscope image data that indicates a position of PFE delivery instrument 200 relative to one or more anatomical features of patient 30 (e.g., a position within the nasal cavity). In this example, the machine learning model can process the endoscope image data to determine whether to enable the output of PFE, whether to cease delivery of PFE, determine one or more parameters of delivered PFE pulses, whether to deliver PFE that achieves neurostimulation, or any combination thereof.

Optionally, the machine learning model stored by control console 100 and/or cloud server 90 can also supplement or overlay information onto an image displayed by endoscope system 80 to assist a clinician in performing one or more procedures. For example, the machine learning model can process data corresponding to parameters of PFE delivered by PFE delivery instrument 200 and dimensions of PFE delivery instrument 200 to determine one or more parameters of a PFE field of the PFE delivered by PFE delivery instrument 200. For example, based on a size of a PFE electrode 206 of PFE delivery instrument 200 and a frequency and magnitude of the PFE pulses, the machine learning model can determine dimensions (e.g., radius) of the PFE field extending outward from the PFE electrode. Also, upon input of the endoscope image data (described above), the machine learning model can automatically modify the displayed medical image at the endoscope to include an overlay the PFE field in real time (with the determined size being proportional to the size of the anatomic features in the endoscope image data), allowing the clinician to see how far the PFE field is reaching relative to anatomical features of patient 30. System 10 is not limited to using a machine learning model to determine the PFE field. System 10 can, in some embodiments, use a computer-implemented software program to determine the PFE field without using a machine learning model.

In some embodiments, the machine learning model stored by control console 100 and/or cloud server 90 can process endoscope image data collected by endoscope system 80 to determine whether to deliver PFE. For example, the machine learning model can determine, based on the endoscope image data, whether the PFE delivery instrument 200 is positioned in a targeted region. Based on whether the PFE delivery instrument 200 is positioned in a targeted region, the machine learning model can control PFE delivery instrument 200 to deliver PFE or control PFE delivery instrument 200 not to deliver PFE. The machine learning model can, based on the endoscope image data, determine one or more parameters of PFE pulses, determine whether to cause neurostimulation by delivering PFE, determine whether to cease delivering PFE, or any combination thereof.

PFE delivery instrument 200 can deliver PFE to a targeted tissue by allowing replacement of diseased cells with normal healthy cells, causing healthy tissue restoration, providing submucosal treatments, and delivering neurostimulation to restore ordinary nerve electrical activity of the nerves proximate to the distal tip 204 of PFE delivery instrument 200. System 10 including PFE delivery instrument 200 can access cavities such as the paranasal sinuses and other areas of the ear, nose, and throat to deliver PFE for treatment of polyps, airflow obstruction, mucus hypersecretion, and other conditions, of PFE delivery instrument 200 is configured to communicate with the control console 100, so that generator 130 can deliver PFE pulses based on a configuration of PFE delivery instrument 200. Configurations of the PFE electrode(s) along the distal tip 204 of PFE delivery instrument 200 include dome tip, basket, or other forms of end effector configurations such as an expandable stent structure for the output of PFE therapy to the targeted tissue.

Figure 4:
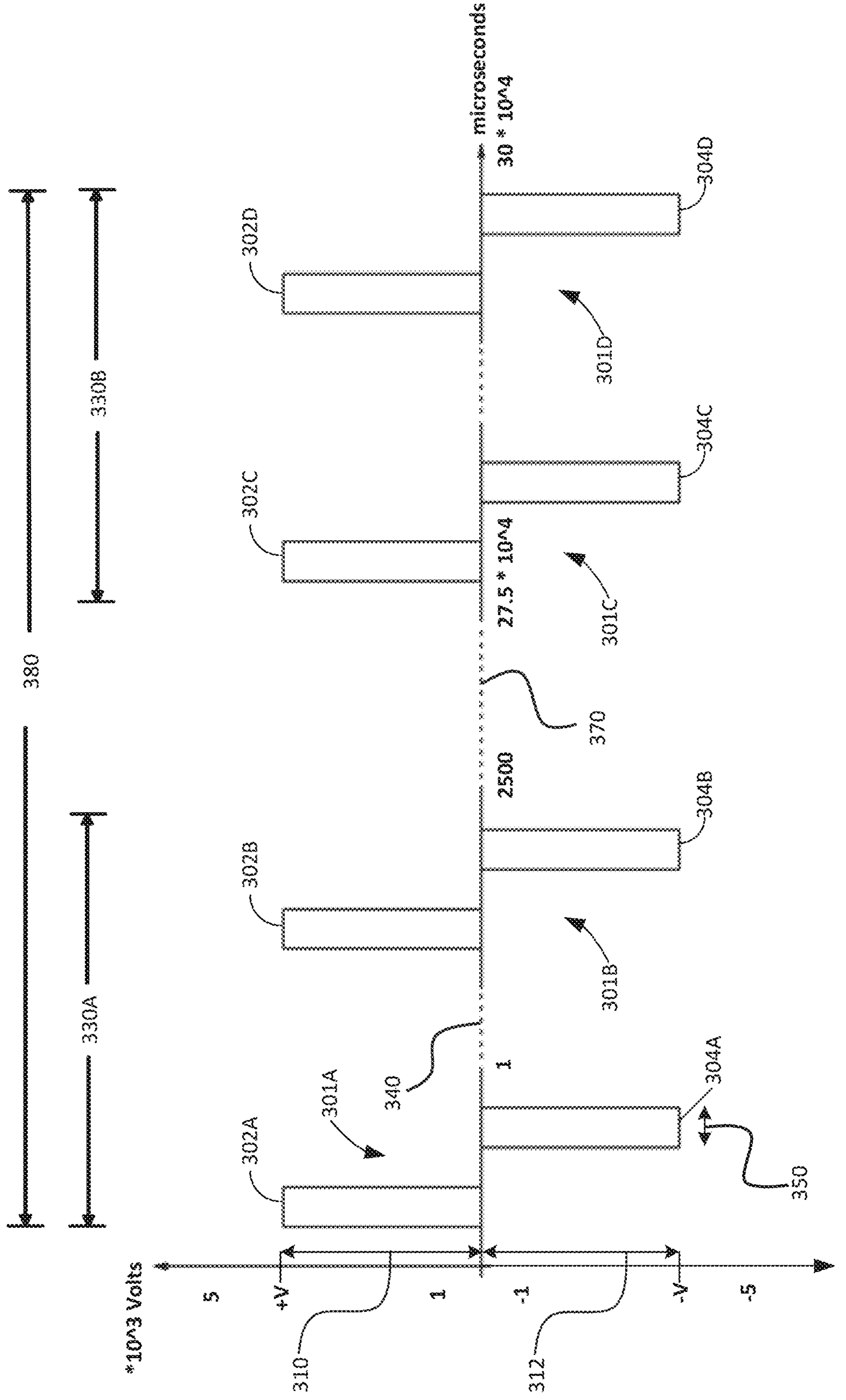
FIG. 4 shows an example of PFE waveforms output by the system of FIG. 1, in accordance with some embodiments.

Referring now to FIG. 4, some embodiments of the PFE control console 100 is configured to output a pulsed field waveform to the PFE delivery instrument 200 so as to deliver a plurality of PFE pulses 301A-301D (collectively, "PFE pulses 301"). PFE delivery instrument 200 can be advanced to a targeted site having diseased tissue which may need to be treated. Generator 130 can output a plurality of PFE pulses via PFE delivery instrument 200. In some embodiments, each PFE pulse of the plurality of PFE pulses can be defined by one or more parameters. For example, a PFE pulse can have an amplitude and a duration, and a sequence of PFE pulses can have a frequency. PFE pulses can, in some embodiments, define a shape. Square pulses, for example, can increase rapidly from a first amplitude to a second amplitude, remain at the second amplitude for the duration of the pulse, and rapidly decrease from the second amplitude to the first amplitude.

In some embodiments, control console 100 can control aspects of the plurality of PFE pulses. For example, control console 100 can control an amplitude of the plurality of PFE pulses, control a frequency of the plurality of PFE pulses, control one or more other parameters of the plurality of PFE pulses, and control whether PFE delivery instrument 200 delivers PFE pulses. PFE delivery instrument 200, in some examples, is configured to deliver PFE pulses 301 to induce electroporation (e.g., irreversible electroporation or reversible electroporation) in a targeted tissue. To induce electroporation, control console 100 can control generator 130 to output pulses at a very high frequency over certain periods of time.

PFE delivery instrument 200 can induce electroporation by applying an electric field to targeted tissue increase a permeability of cell membranes of the targeted tissue. High frequency electrical signals can induce electroporation through a phenomenon called dielectric heating. Dielectric heating can occur when electrical signals are applied to tissue. Rapid changes in the electric field cause water molecules within the cells to re-align with the changing electrical field. This rapid realignment of water molecules can generate heat due to molecular friction, causing a localized increase in temperature. This increase in temperature can cause pores to temporarily form in the cell membrane. High frequency electrical signals can be effective at inducing electroporation because the high frequency switching between voltages can excite the water molecules to form the pores.

As described above, there are at least two different kinds of electroporation that PFE delivery instrument 200 can deliver including irreversible electroporation and reversible electroporation. PFE delivery instrument 200 can deliver PFE pulses 301 to induce irreversible electroporation via apoptosis through several mechanisms. For example, PFE pulses 301, when delivered to targeted tissue, can disrupt cellular homeostasis by disrupting a balance of ions and molecules within cells of the targeted tissue. This can lead to changes in intracellular pH and changes in calcium levels in the cells of the targeted tissue. These disruptions can trigger signaling pathways that ultimately lead to apoptosis. Example signaling pathways include the intrinsic pathway and the extrinsic pathway. Formation of pores in the cell membrane associated with irreversible electroporation can also damage to cellular structures such as organelles and the cytoskeleton. This damage can activate cellular stress responses that initiate apoptotic pathways.

In some embodiments, PFE delivery instrument 200 can deliver PFE pulses 301 to induce reversible electroporation by causing pores to temporarily form in cell membranes of the targeted tissue without causing the cells to eventually die through apoptosis. Control console 100 can dictate whether PFE delivery instrument 200 induces irreversible electroporation or reversible electroporation by controlling parameters of PFE pulses 301. For example, PFE pulses that induce reversible electroporation are typically shorter and less intense than PFE pulses that induce irreversible electroporation. Other parameters such as pulse frequency can influence whether PFE pulses induce reversible electroporation or irreversible electroporation.

Any heat associated with electroporation induced by PFE pulses 301 is momentary and thus results in a little or no temperature change at the targeted tissue (i.e., a "nonablative temperature change" of 0 to 5 degrees C.) and thus safely avoids the type of necrosis resulting from thermal ablation techniques. This is because PFE delivery instrument 200 can deliver PFE pulses 301 so that a high frequency electrical signal is delivered to tissue for no more than a threshold amount of time. Limiting the amount of time that tissue is exposed to the PFE signal limits a heat increase associated with the electrical stimulation therapy approach. PFE delivery instrument 200 may control PFE pulses 301 based on a selected electroporation effect (e.g., selecting either reversible electroporation or irreversible electroporation), and furthermore based on a procedure being performed by PFE delivery instrument 200. In some embodiments, PFE delivery instrument 200 can control PFE pulses 301 based on user input. Optionally, PFE delivery instrument 200 can control PFE pulses 301 based on a machine learning model or another kind of model.

In the embodiment illustrated in FIG. 4, each of PFE pulses 301 represents a biphasic pulse having a positive phase followed by a negative phase. For example, PFE pulse 301A includes positive phase 302A and negative phase 304A, PFE pulse 301B includes positive phase 302B and negative phase 304B, and so on. The magnitude of the negative phase of each of PFE pulses 301 can be equal to the magnitude of the positive phase of each of PFE pulses 301. For example, the amplitude 310 of each of positive phases 302A-302D can be +V and the amplitude 312 of each of negative phases 304A-304D can be −V. This means that for each of PFE pulses 301 the magnitude of the positive phase is the same as the magnitude of the negative phase, and preferably the magnitude is a high voltage magnitude of at least 850V. In some examples, each individual pulse may vary for +V within a range from 850V to 10,000V. In some examples, each individual pulse may vary for −V within a range from −850V to −10,000V. As shown in FIG. 4, there can be a gap between a positive phase and a negative phase of a biphasic PFE pulse. This gap is not necessarily present in every embodiment. In some embodiments, biphasic and/or triphasic PFE pulses can include no gap between pulse phases. In some embodiments, a pulse width 350 of each individual phase of PFE pulses is less than 5 microseconds (μs), and preferably within a range from 50 nanoseconds (ns) to 3 μs.

In some embodiments, PFE pulses 301 preferably include biphasic pulses. This is because monophasic pulses delivered to the targeted tissue can cause muscle contraction to a greater degree as compared with muscle contraction caused by biphasic pulses cause muscle contraction. In some embodiments, PFE delivery instrument 200 can deliver biphasic PFE pulses without causing any muscle contraction. It may be beneficial to deliver PFE pulses 301 without causing muscle contraction, as muscle contraction could cause patient movements that disrupt the procedure. Another advantage of biphasic pulses is that biphasic pulses have a balanced charge distribution which prevents accumulation of charge at an interface between PFE electrode 206 and the targeted tissue. Such charge accumulation can damage tissue and/or cause the patient discomfort.

PFE delivery instrument 200 is not limited to delivering biphasic PFE pulses. In some embodiments, PFE delivery instrument 200 can deliver one or more monophasic PFE pulses. In some cases, PFE delivery instrument 200 can deliver one or more triphasic PFE pulses. In some cases, PFE delivery instrument 200 can deliver a mixture of any combination of monophasic, biphasic, and triphasic pulses. Control console 100 can control a number of phases of the PFE pulses delivered by PFE delivery instrument 200.

PFE pulses 301, in some examples, include a sequence of bursts of high-frequency pulses. Each burst of high-frequency pulses can include a pulse train at a high frequency. For example, pulse train 330A includes PFE pulse 301A through PFE pulse 301B. Although FIG. 4 illustrates pulse train 330A and pulse train 330B as each including only two pulses, pulse train 330A and pulse train 330B can each include significantly greater than two pulses. For example, pulse train 330A can include one or more pulses within gap 340 between pulse 301A and pulse 301B and pulse train 330B can include one or more pulses within gap 342 between pulse 301C and pulse 301D. In some examples, each of pulse train 330A and pulse train 330B can include within a range from 10 pulses to 500 pulses. Preferably, each cycle of PFE delivery 380 pulse train 330A, pulse train 330B, and other trains after 330B may preferably include approximately 2,500 pulses in total. Although FIG. 4 illustrates only two pulse trains 330A and 330B, PFE delivery instrument 200 can deliver more than two pulse trains (e.g., one or more pulse trains between pulse train 330A and pulse train 330B.

In some embodiments, pulse train 330A and pulse train 330B may each define a pulse frequency within a range from 500 kilohertz (kHz) to 10,000 kHz. The pulse frequency of each of pulse train 330A and pulse train 330B can induce electroporation (e.g., irreversible electroporation in this embodiment) in targeted tissue. Control console 100 can, in some examples, control the frequency of each of pulse train 330A and pulse train 330B to achieve a desired effect (e.g., perform a certain procedure). Within each of pulse train 330A and pulse train 330B, there may be a gap such as the method of treatment is primarily associated with apoptosis and secondary with stimulation delivered. duration of the gap Since pulse train 330A and pulse train 330B comprise high-frequency bursts of PFE pulses, the gap between consecutive PFE pulses within a pulse train can be very short. This rapid transition between each pulse can induce electroporation while inducing some neurostimulation effects.

PFE delivery instrument 200 can deliver a sequence of pulse trains 380 including pulse train 330A and pulse train 330B. In some examples, the sequence of pulse trains 380 can include pulse trains at a pulse train frequency. The pulse train frequency can be within a range from 1 hertz (Hz) to 100 Hz. This means that the frequency at which PFE delivery instrument 200 delivers pulse trains of the sequence of pulse trains 380 can be orders of magnitude lower than the frequency at which PFE delivery instrument 200 delivers PFE pulses within a particular pulse train. As a result, there can be gaps between consecutive pulse trains of the sequence of pulse trains 380 that are significantly longer than gaps between consecutive PFE pulses within a pulse train. In some examples, a duration of a gap between consecutive pulse trains is within a range from 0.005 seconds to 1 second.

Accordingly, in particular implementations of the PFE console 100, by delivering the sequence of pulse trains 380 including gaps between pulse trains, PFE delivery instrument 200 can be used at the targeted tissue to induce electroporation without changing the temperature of the targeted tissue by more than 5-degree C. and thus safely avoiding the type of ablative necrosis/crusting caused by RF ablation and other thermal ablation techniques. For example, the PFE console 100 can control the sequence of pulse trains 380 (and the gaps therebetween) to avoid sustained delivery of high frequency electrical signals that might otherwise excite water molecules within cells in a way that releases a significant amount of heat to induce necrosis. Instead, the PFE console 100 can limit each of the pulse trains 380 to less than a threshold duration and provide gaps between consecutive pulse trains to thereby allow PFE delivery instrument 200 to induce electroporation (which can trigger cellular apoptosis and thus replace the diseased/faulty cells with healthy cells).

Still referring to FIG. 4, the PFE delivery instrument 200 can also stimulate one or more nerves proximate the targeted tissue. By delivering the sequence of pulse trains 380 including gaps between pulse trains, PFE delivery instrument 200 can allow action potentials to develop within the nerves and propagate along the nerves proximate the targeted tissue. This means that by delivering PFE pulses 301, PFE delivery instrument 200 can optionally deliver neurostimulation to the patient in addition to inducing electroporation in targeted tissue of the patient. In some cases, the lower frequency at which PFE delivery instrument 200 delivers the sequence of pulse trains 380 is more effective for stimulating nerves as compared with the higher frequency at which PFE delivery instrument 200 delivers the PFE pulses within each pulse train. This is because neurostimulation involves inducing action potentials within nerves that propagate following stimulation. Constant, high-frequency stimulation does not necessarily allow action potentials to take hold.

Accordingly, referring to FIGS. 1-4, the PFE control console 100 can configure one or more PFE parameters such as a number of PFE pulses per pulse train, pulse amplitude, pulse duration, a frequency at which PFE pulses occur within a pulse train, and a frequency at which pulse trains occur. Control console 100 can configure parameters of PFE pulses 301 depending on a procedure performed by PFE delivery instrument 200. In some embodiments, control console 100 can deliver PFE pulses 302 via PFE electrode 206 to treat the targeted tissue by simultaneously inducing irreversible electroporation and delivering neurostimulation. It is not required for PFE delivery instrument 200 to simultaneously induce irreversible electroporation and deliver neurostimulation. In some cases, PFE delivery instrument 200 can induce irreversible electroporation without delivering neurostimulation. In some cases, PFE delivery instrument 200 can deliver neurostimulation without inducing irreversible electroporation.

In some embodiments, control console 100 can apply a predetermined electric field to the targeted tissue in a rapid pattern that induces cell membrane destabilization at the targeted tissue. PFE electrode 206 can work in conjunction with the grounding electrode pad 60 mounted to the patient's body. For example, PFE electrode 206 can deliver PFE pulses. The PFE pulses can travel from PFE electrode 206 to grounding electrode pad 60, which serves as a return electrode. It is not required for system 10 to use grounding electrode pad 60 as a return electrode. PFE electrode 206 can deliver PFE pulses without any return electrode. System 10 can alternatively use a return electrode other than grounding electrode pad 60. For example, a return electrode can be located on a shaft separate from PFE delivery instrument 200, the shaft being advanced to a site proximate the targeted tissue. When the PFE delivery instrument 200 delivers PFE pulses, the pulses can return via the return electrode on the separate shaft. As described in more detail below, the PFE delivery instrument 200 can be advanced to a targeted anatomical space while under medical imaging, for example using the endoscope system 80 including a handheld endoscope instrument 50 configured to be handled by the user simultaneously with PFE delivery instrument 200.

As described in more detail below, in some embodiments, control console 100 can selectively enable PFE output from the generator 130 in response to detecting certain anatomical landmarks. For example, control console 100 can detect anatomical landmarks corresponding to targeted tissue for a procedure and enable PFE in response to detecting these landmarks. The control console 100 can communicate (e.g., via a wired or wireless connection to the internet) with the cloud server 90 to transmit data from the control console 100 to the cloud server 90.

PFE generator 130 of the control console 100 can be configured to output a variety of PFE from the PFE electrode 206. In some embodiments, the PFE pulses output by the generator 130 and delivered from the PFE delivery instrument 200 provides an electric field that is applied to the targeted tissue in a series of rapid bursts to cause electroporation at the targeted tissue, thereby inducing cell membrane destabilization to trigger apoptosis while also maintaining substantially no temperature change at the targeted tissue (e.g., a temperature change of less than 5 degrees C.). Optionally, the PFE energy output by the generator 130 and delivered from the instrument 200 can provide highly effective treatment at the targeted tissue within an car, nose, or throat while achieving improved convenience for both the clinician and the patient. For example, PFE delivery instrument 200 can deliver therapy while patient 30 is awake and using a local topical anesthetic instead of a general anesthetic.

Figure 5:
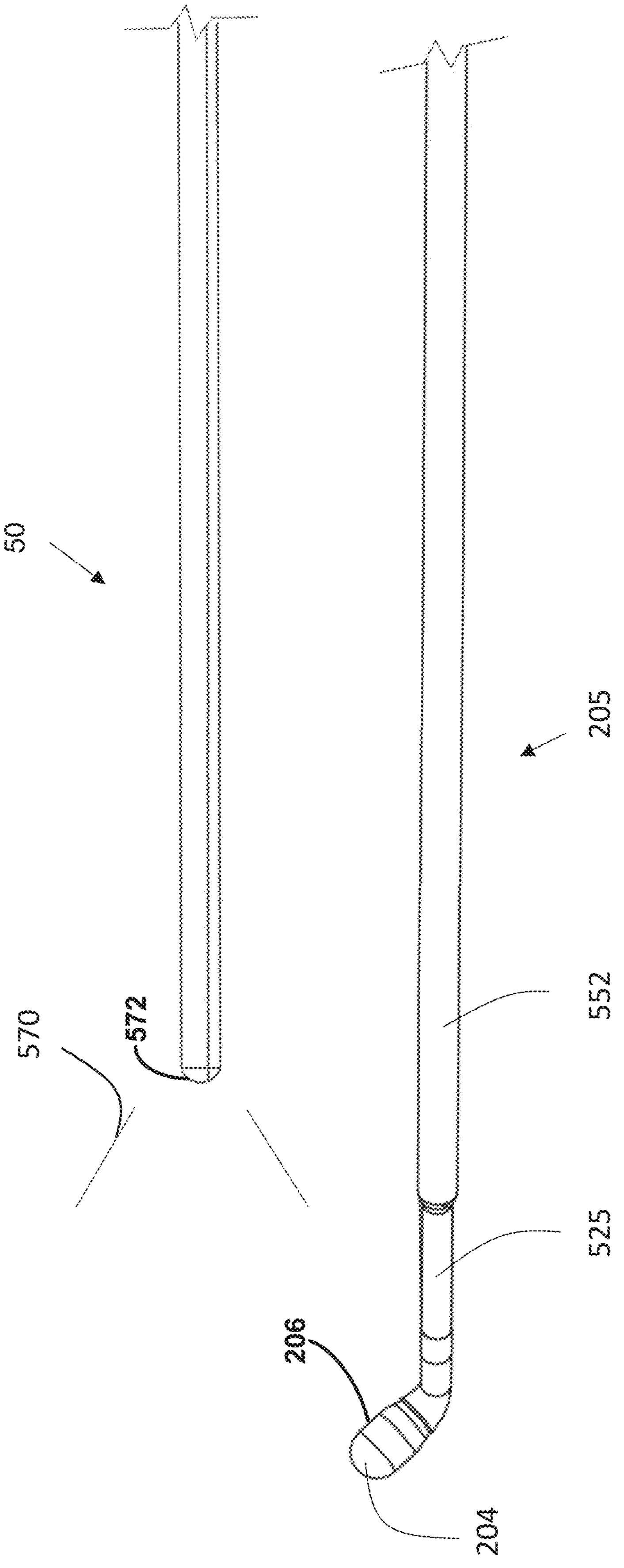
FIG. 5 shows a side view of a distal portion of a PFE delivery instrument and a side view of a distal portion of an endoscope of the system of FIG. 1.

Referring now to FIG. 5, some embodiments of the PFE delivery instrument 200 can be used in combination with using endoscope instrument 50. For example, in use, the PFE delivery instrument 200 is advanced to the targeted tissue and endoscope instrument 50 is also advanced so that a location of the targeted tissue relative to distal tip 204 is within the field of view 570 of endoscope instrument 50. In some embodiments, endoscope instrument 50 includes an endoscope lens 572 placed on a distal tip of endoscope instrument 50 This means that the location of the targeted tissue relative to distal tip 204 can be displayed in real time by a display screen of endoscope system 80. As shown in FIG. 5, some implementations of the PFE instrument include the distal tip 204 having a bulbous shape (having a rigid structure and a fixed size) that provides a lateral width greater than an outer diameter of the elongated shaft 205 from which the distal tip 204 extends.

Elongated shaft 205 of PFE delivery instrument 200, in some embodiments, includes a rigid straight shaft 552 and a bendable distal shaft portion 525 that is axially transverse from the rigid straight shaft 552. In the embodiment illustrated in FIG. 5, the bendable distal shaft portion 525 extends distally from a distal end of the straight shaft 552. Optionally, the bendable distal shaft portion 525 can be preconfigured to a fixed bent shape such that bent distal portion 525 does not deform from the bent shape. Alternatively, in the embodiment of FIG. 5, the distal shaft portion 525 is manually bendable and repeatably deformable to a user-selected bent orientation relative to the rigid straight shaft 552. As such, an angle of the bendable distal shaft portion 525 is manually adjustable to customize the bendable distal shaft portion 525 to a relative position that is selected for the anatomy of a particular patient. In some optional embodiments, PFE delivery instrument 200 can include an actuator along its proximal handle region (FIG. 3) that allows user 20 to adjust an angle of bendable distal shaft portion 525 during a procedure to deliver PFE to targeted tissue. For example, the actuator can be slidable along a longitudinal axis of the handle. As the actuator slides, this can adjust the angle of the bendable distal shaft portion 425. As shown in FIG. 5, the distal tip 204 can have a bulbous shape such that provide an outer diameter of the PFE electrode is greater than a maximum outer diameter of the shaft portion 525 that extends toward the tip 204.

In some examples, bendable distal shaft portion 525 having the angle illustrated in FIG. 5 (transverse to a longitudinal axis of the rigid straight shaft 552) represents an improved system that ensures distal tip 204 is within the field of view 570 of endoscope instrument 50. For example, the field of view 570 of endoscope instrument 50 can capture the distal tip 204 without capturing other portions of PFE delivery instrument 200, meaning that because distal shaft portion 525 is bent to an orientation offset from a central axis of the straight shaft 552, this improves an ability of endoscope instrument 50 to capture bent distal shaft portion 525 within its field of view 570.

In the embodiment shown in FIG. 5, PFE delivery instrument 200 includes a single, fixed-size monopolar PFE electrode 206 configured to deliver the PFE therapy. In some cases, systems that use monopolar electrodes also use a separate a return electrode (e.g., grounding electrode pad 60 in FIG. 1) placed on the patient's body or near the patient's body. Return electrodes can, in some cases, prevent unwanted current from passing through sensitive tissues. The monopolar electrode 206 of the instrument 200 can be useful for delivery of PFE therapy with high voltage electrical signals (such as the PFE pulses 302 in FIG. 4). For example, in some circumstances, the monopolar electrode 206 can be configured to avoid arcing during the output of such high voltage electrical pulses, which is potentially damaging to tissue adjacent the instrument. Thus, as shown in FIG. 1, the PFE delivery instrument 200 includes a monopolar PFE electrode 206 that can work in conjunction with the grounding electrode 60 (spaced sufficiently apart from the distal tip of the PFE delivery instrument 200), thereby reducing the likelihood of arcing. In some alternative embodiments, the PFE delivery instrument 200 can include bipolar electrodes that work in conjunction with one another during treatment.

In some examples, PFE electrode 206 comprises a conductive surface exposed along an exterior surface of the distal tip 204 of the PFE delivery instrument 200. In some embodiments, PFE electrode 206 does not extend outward away from the housing of PFE delivery instrument 200. PFE electrode 206 can be connected to a conductor which extends through a lumen of PFE delivery instrument 200. In some examples, the conductor can connect to control console 100 (e.g., via connector 208 in FIG. 3). In some examples, bendable distal shaft portion 525 and elongated shaft 205 are sized to navigate to targeted tissue within the patient (e.g., locations within the ear, nose, and throat. For example, the bendable distal shaft portion 525 can have an outer shaft diameter that is smaller than that of the elongated shaft 205 and smaller than a maximum lateral width of the distal tip 204. In other words, in this example, the maximum lateral width of the distal tip 204 is greater than the outer shaft diameter of both the bendable distal shaft portion 525 and the elongated shaft 205. In the embodiment depicted in FIG. 5, the bendable distal shaft portion 525 can have an outer shaft diameter of 1 mm to 3 mm, and preferably about 1.5 mm, and the elongated shaft 205 can have an outer shaft diameter of 1.5 mm to 4 mm, and preferably about 2 mm. Also, in the embodiment depicted in FIG. 5, the maximum lateral width diameter of the distal tip 204 of the PFE delivery instrument 200 can less than 5 mm, preferably 2 mm to 4 mm, and about 3 mm in this embodiment. As such, PFE delivery instrument 200 can navigate to the targeted tissue so that PFE electrode 206 is proximate the targeted tissue and without anatomy of the patient obstructing advancement of PFE delivery instrument 200.

Referring now to FIGS. 6A-8B, some alternative embodiments of the PFE delivery instrument 600, 700, 800 can include a flexible PFE electrode having a metallic mesh or basket structure. For example, the embodiments of the flexible PFE electrode depicted in FIGS. 6A-8B can be compressed during delivery and then flexibly expand to have a larger radius to provide an electrode shape that compressed against the targeted tissue, which can be useful in some implementations for anchoring the distal tip of the PFE delivery instrument 600, 700, 800 in place during the PFE treatment. The flexible PFE electrode located on the treatment tip may adapt and conform to the inner walls of the targeted anatomical passageway such as the nasal cavity.

Figure 6A:
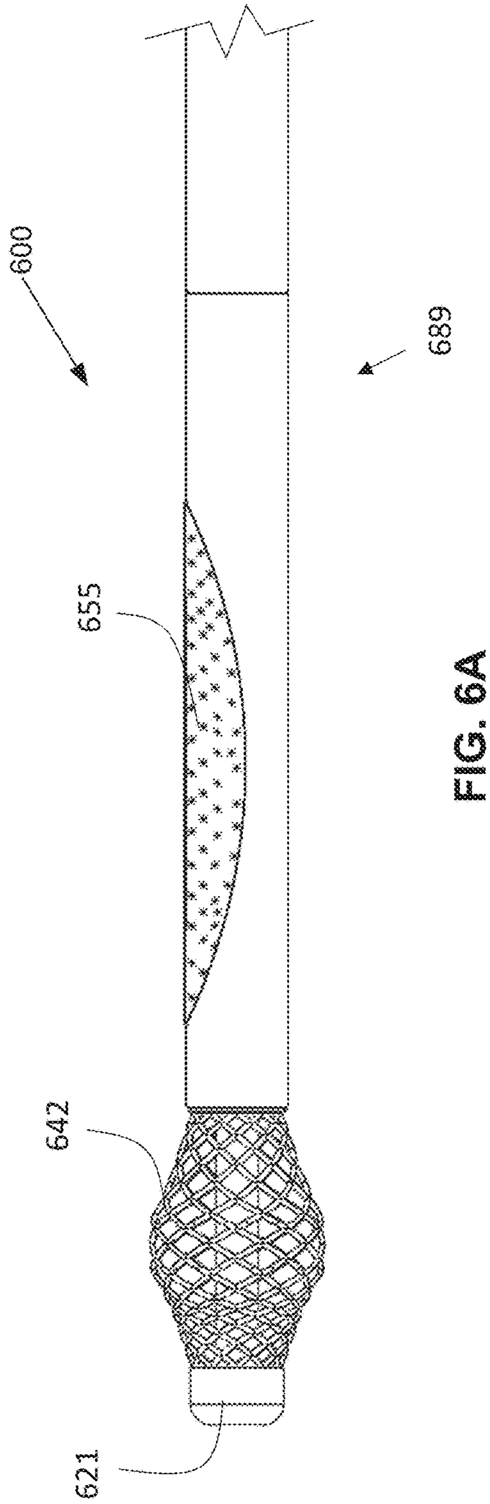
FIGS. 6A-6B show side views of distal portions of a PFE delivery instrument, optionally for use with the system of FIG. 1, in accordance with some alternative embodiments.
Figure 6B:
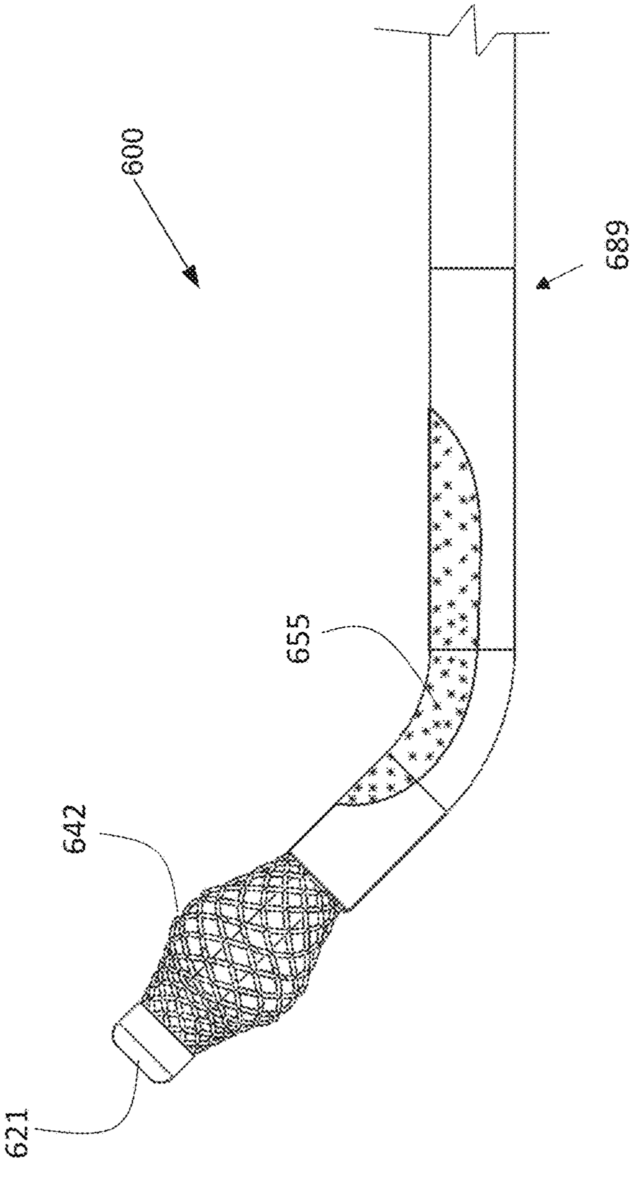

As shown in FIGS. 6A-6B, an elongated shaft 689 of a PFE delivery instrument 600 can include a flexible PFE electrode 642 in the form of a metallic basket electrode positioned at a distal end of an elongated shaft 689. The basket electrode 642 can operate as a PFE electrode that, in some embodiments, is spring biased to have a larger maximum lateral width than that of the elongated shaft 689. For example, the basket electrode 642 can flexibly adjust such that it is compressed toward a central axis of the elongate shaft 689 (e.g., during delivery into a nose), yet the basket electrode 642 is spring biased to outwardly expand (at least at its central region) such that it is urged against a wall of the targeted anatomical passageway such as the nasal cavity. In some examples, basket electrode 642 comprises a plurality of spiral-shaped struts, the diameter of the spirals being enlarged at a center of the struts. Each spiral-shaped strut can connect with other struts at connection points such that the plurality of struts of basket electrode 642 form a single piece of conductive material defining a plurality of open cells. In some embodiments, it is beneficial for PFE delivery instrument 600 to include a basket electrode 642, for example, so as to increase the overall electrode surface area and thereby disperse high-voltage pulses (e.g., FIG. 4) to a greater volume of tissue as compared with a smaller fixed-ring electrode. Thus, optionally, the basket electrode 642 can be advanced to the targeted tissue and deliver a large amount of PFE over a larger anatomical space, including for delivery of PFE therapy for treatment of nasal valve collapse.

In some embodiments, the PFE instrument 600 can be equipped with two or more types of electrodes. For example, the PFE instrument 600 can include both a distal tip electrode 621 and the basket electrode 642, which can be used simultaneously or in isolation. As such, the basket electrode 642 can be advanced to the targeted tissue and the generator 130 (FIGS. 1-2) can activate PFE delivery via the fixed-ring of the distal tip electrode 621, via the flexible basket electrode 642, or both. The instrument 600 can be configured such that a switch along the handle (not shown; refer to the example handle depicted in FIG. 3) is configured for the user to select which electrode or combination of electrodes will output the PFE therapy.

Still referring to FIG. 6A-6B, the flexible PFE electrode 642 can comprise a conductive flexible material such as stainless steel, titanium, iridium, aluminum, gold, silver, nitinol, nickel, or any alloy, composition, or combination of these materials. In some embodiments, basket electrode 642 is shaped to deliver PFE to targeted tissue in a way that improves patient safety and decreases a risk of tissue damage. For example, the basket electrode 642 can be spring biased toward a shape that has a wider center portion that tapers (along a curved circumferential region) toward smaller ends (refer to FIGS. 6A-6B), thereby ensuring that the flexible basket electrode 642 is biased outwardly to conform and compress against the targeted tissue and then rapidly deliver PFE pulses distributed throughout all regions of basket electrode 642 in contact with tissue.

In some embodiments elongated shaft 689 can include a steerable or malleable region 655 that can extend distally from the straight portion of elongated shaft 689 at a transverse angle from a central axis of the straight portion of elongated shaft 689. For example, a portion of elongated shaft 689 including basket electrode 642 and distal tip 621 can be manually bent by a user about malleable region 655 so that the portion including basket electrode 642 forms an angle with a straight portion of elongated shaft 689. In some examples, PFE delivery instrument 600 includes a steering actuator along the handle (not shown; refer to the example handle depicted in FIG. 3) that is configured to selectively adjust the angle of the steerable or malleable region 655. As such, the user 20 (FIG. 1) can controllably maneuver the elongated shaft 689 within anatomical passageways of the patient.

Figure 7:
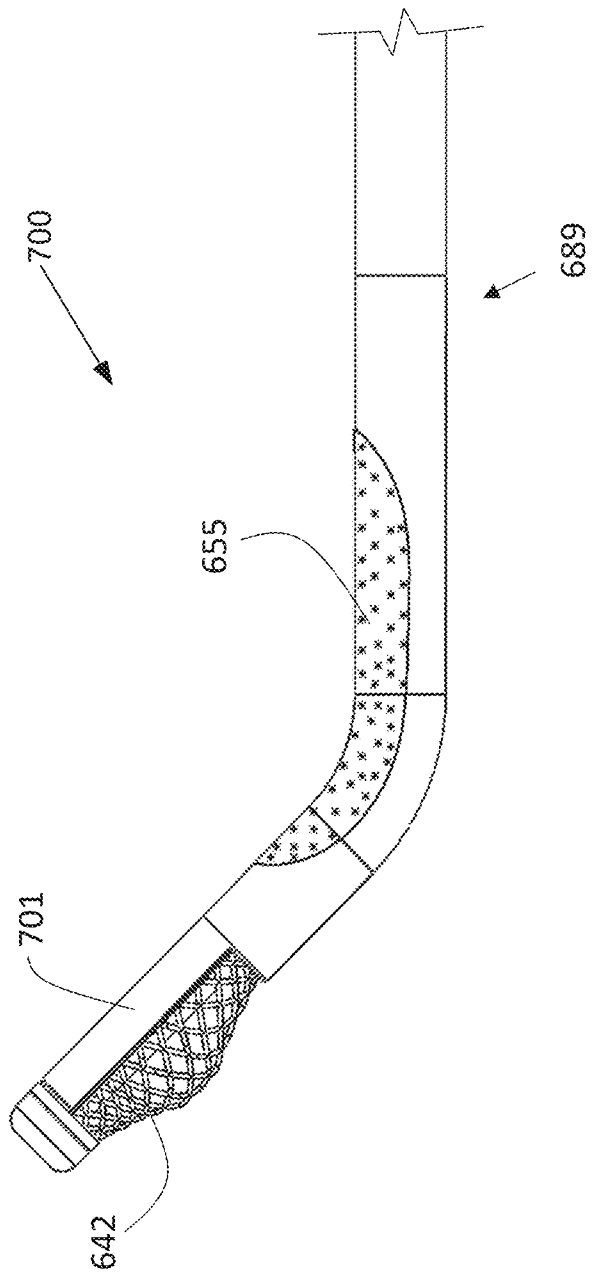
FIG. 7 shows side views of distal portions of another PFE delivery instrument, optionally for use with the system of FIG. 1, in accordance with some alternative embodiments.

Referring now to FIG. 7, some embodiments of the PFE delivery instrument 700 can include a flexible PFE electrode 642 that is partially insulated with an insulative cover 701. In some embodiments, insulative cover 701 comprises a non-conductive element that prevents electrical pulses from crossing insulative cover 701. This means that PVE pulses output from the partially insulated basket electrode 642 (FIG. 7) can be directed in a selected orientation relative to the elongated shaft 689 toward adjacent tissue proximate to the exposed portion of basket electrode 642 (opposite from the insulative cover 701). In some examples, the partially insulated basket electrode 642 with the insulative cover 701 can improve an ability of basket electrode 642 to treat certain targeted tissue regions without delivering therapy to an entire circumferential periphery around the central axis of the electrode 642, thereby enabling the user to shield non-targeted tissue regions from the PFE pulses. For example, when elongated shaft 689 is arranged so that the insulative cover 701 is positioned toward the non-targeted tissue region and the flexible basket electrode 642 is oppositely oriented against the targeted tissue (as verified via the endoscope 50 in FIG. 1), the user can signal the PFE control console 100 to initiate the PFE pulses for treatment of the targeted tissue with simultaneous protection of the non-targeted tissue.

Insulative cover 701 can comprise a non-conductive material such as polyamide, polytetrafluoroethylene (PTFE), glass, ceramic, plastic, rubber or any composition or combination of these materials. Optionally, the cover 701 can removably mated to the elongate shaft 689 so as to provide a shield over a portion of the basket electrode 642. Example procedures in which the partially insulated basket electrode 642 (with insulative cover 701) may be particularly useful include PFE therapy delivered to the palate of a patient who suffers from obstructive sleep apnea (OSA). In these procedures, it can be preferred to treat the soft palate tissue by delivering PFE pulses without delivering PFE pulses to the tongue region (which is shielded using the insulative cover 701).

Figure 8A:
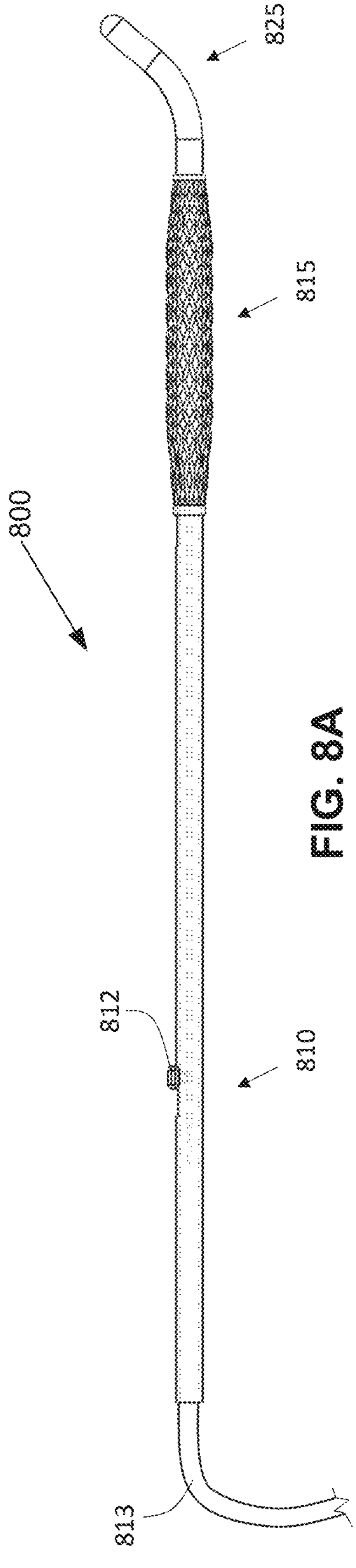
FIGS. 8A-8B show side views of distal portions of another PFE delivery instrument, optionally for use with the system of FIG. 1, in accordance with some alternative embodiments.
Figure 8B:
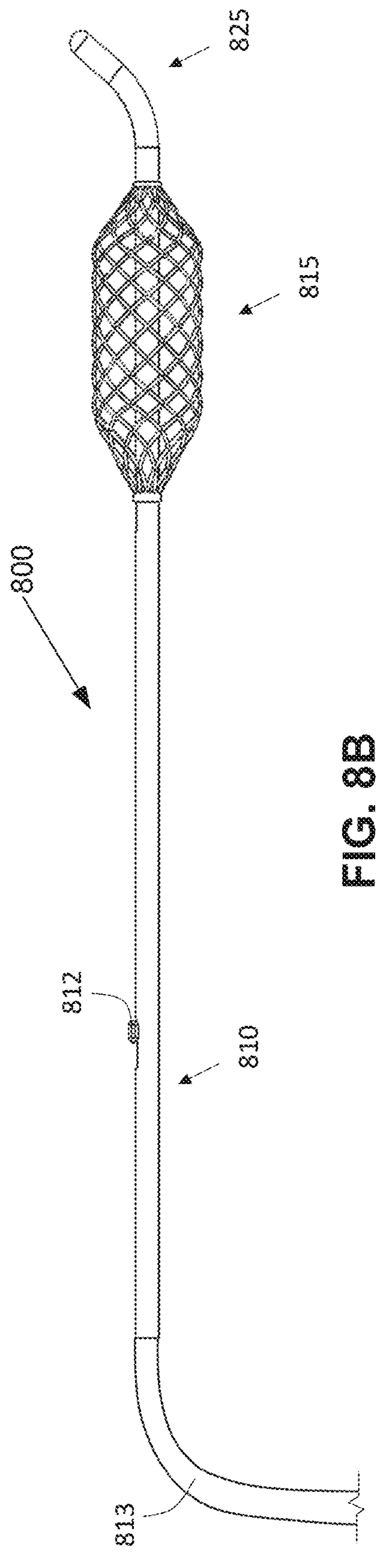

Referring now to FIGS. 8A-8B, some embodiments of the PFE delivery instrument 800 can include an expandable stent PFE electrode 815 that is manually actuatable between a collapsed condition (FIG. 8A) and an expanded condition (FIG. 8B). For example, the expandable stent FE electrode can be advanced toward a narrow anatomical passageway in an car, nose, or throat while the electrode 815 is in the collapsed condition (FIG. 8A), and then the user can adjust the electrode 815 to the expanded condition using the slider actuator 812 when stent electrode 815 is proximate target tissue (thereby urging the flexible PFE electrode 815 to outwardly conform to the targeted tissue and increase the electrode-tissue surface contact). In some examples, the PFE delivery instrument 800 can include a distal portion 810 having a smaller diameter that is sized to allow the instrument to reach narrow anatomical passageways such as the Eustachian tube via the middle car, the middle car plexus, and other regions of consisting of narrow anatomy.

Optionally, the distal portion 810 can include a bent tip 825, which can be manually bendably by a user prior to the procedure and/or bent during the procedure. As seen in FIGS. 8A-8B, the expandable stent PFE stent electrode 815 can be located on a straight part of distal portion 810, and the bent tip 825 extends distally from a distal end of the expandable stent PFE electrode 815. In some embodiments, it can be preferred to manually bend the bent tip 825 to a selected deformation/orientation prior to advancing distal portion 810 to targeted tissue. This can allow user 20 to guide the instrument during advancement by rotating the distal portion 810 to engage the bent tip 825 with a narrow anatomical passageway including the targeted tissue. When the passageway is engaged, the distal portion 810 can be advanced until the stent electrode 815 is placed within the area where the PFE can be delivered. The stent electrode 815, initially collapsed, can be expanded using the actuating slider 812 when stent electrode 815 is proximate target tissue. Bent tip 825 can be bent either by mechanically deforming the distal end of the tip, at the manufacturing facility by design where the tip is made pre-bent, or by having an automated motorized or mechanical pull actuator on the handle.

Figure 9:
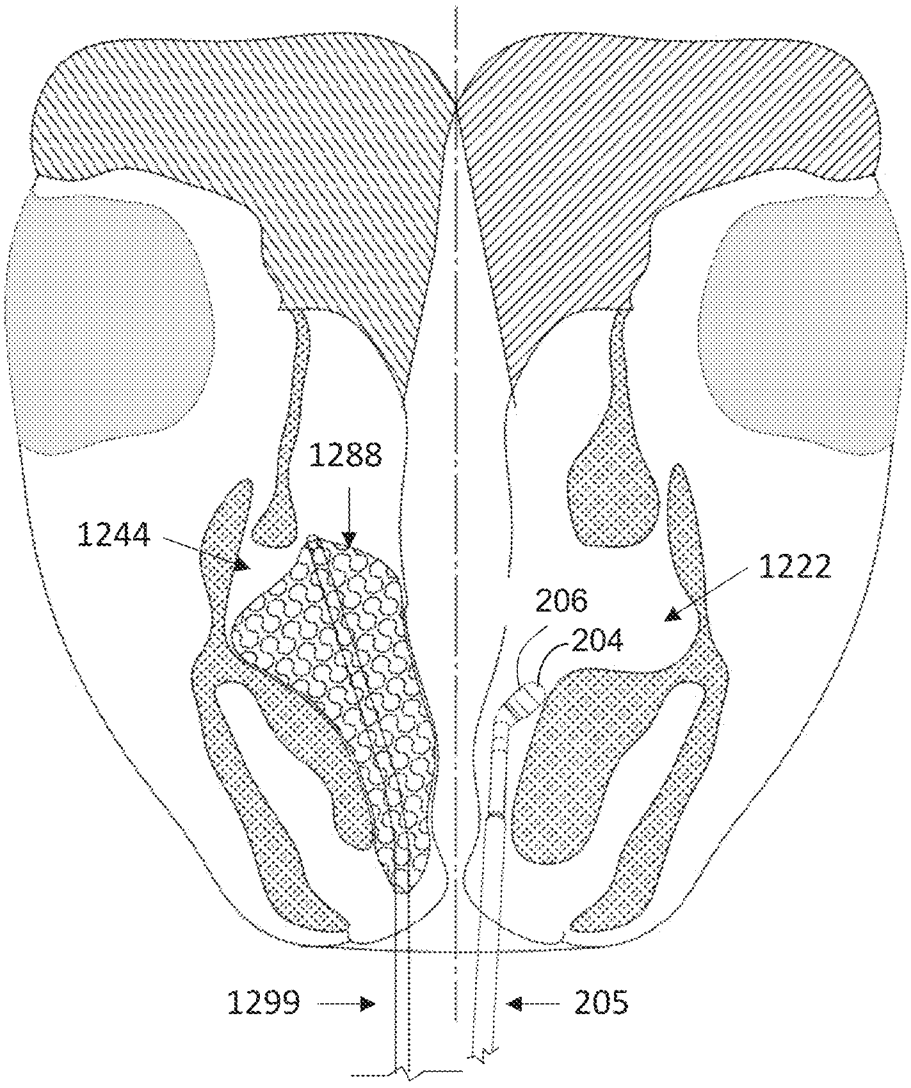
FIG. 9 shows a sectional view of a nasal region having therein the PFE delivery instrument of the system of FIG. 1 and an optional return electrode, in accordance with some embodiments.
Figure 10:
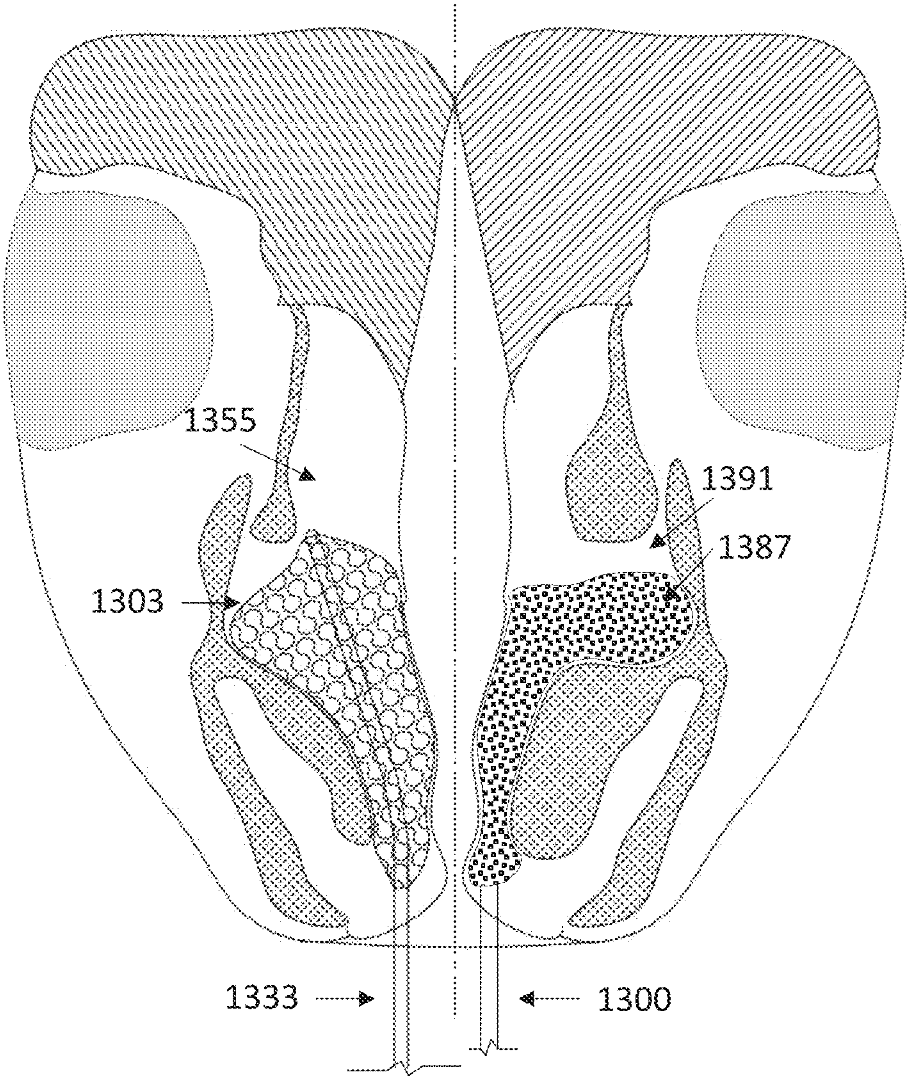
FIG. 10 shows a sectional view of a nasal region having therein another PFE delivery instrument with a bipolar electrode configuration, optionally for use with the system of FIG. 1, in accordance with some alternative embodiments.

Referring now to FIGS. 9-10, some embodiments of the PFE delivery instrument 200 (or 600, 700, or 800) can be configured to operate in conjunction with a shaft-mounted grounding electrode 1288. In such cases, the grounding electrode 1288 can be directed toward a selected portion of an anatomical cavity (rather than an external grounding pad 670 as depicted in FIG. 1). As such, the PFE delivery instrument 200 can deliver PFE pulses via the PFE electrode 206 (as described in FIGS. 3-4 above) while a lead 1299 including the return electrode 1288 (having a flexible mesh structure in the depicted embodiment) is positioned within the body at a location proximate targeted tissue. In this embodiment, the electrode mesh 1288 provides a return electrode having a surface area that is significantly larger than a surface area of PFE electrode 206. This large surface area can reduce a likelihood of arcing between PFE electrode 206 and mesh 1288.

In the example illustrated in FIG. 9, the PFE electrode 206 and the passive electrode mesh 1288 can both be located within the body. For example, PFE electrode 206 can be located within a first nasal region 1222 and the return electrode 1288 can be located within a second nasal region 1244. Although the embodiment of FIG. 9 includes two electrodes 206 and 1288, the system can include more than two electrodes in some embodiments. For example, there may be more than one circuit between therapy delivery electrodes and return electrodes.

Referring now to FIG. 10, some embodiments of the system can include a first active electrode 1387 attached to a first lead 1300 and a second active electrode 1303 attached to a second lead 1333. Both of the first active electrode 1387 and the second active electrode 1303 can deliver PFE pulses, and both of the first active electrode 1387 and the second active electrode 1303 can be configured as flexible metallic mesh electrodes. First active electrode 1387 and second active electrode 1303 can both be used to deliver PFE pulses in a monopolar configuration or in a bipolar configuration. For example, a monopolar configuration implemented for the output of PFE pulses from the first and second active electrodes 1387 and 1303 where the PFE output involves a uniform electric field instead of a directed current. In procedures where nerves are at least partially responsible for causing symptoms such as chronic rhinitis, tympanic plexus neurectomy for intractable otalgia, trigeminal nerve treatment for migraines, and other diseases, PFE can be beneficial in that PFE can replace faulty cells through apoptosis and restore nerves to a standard function through neurostimulation.

Figure 11:
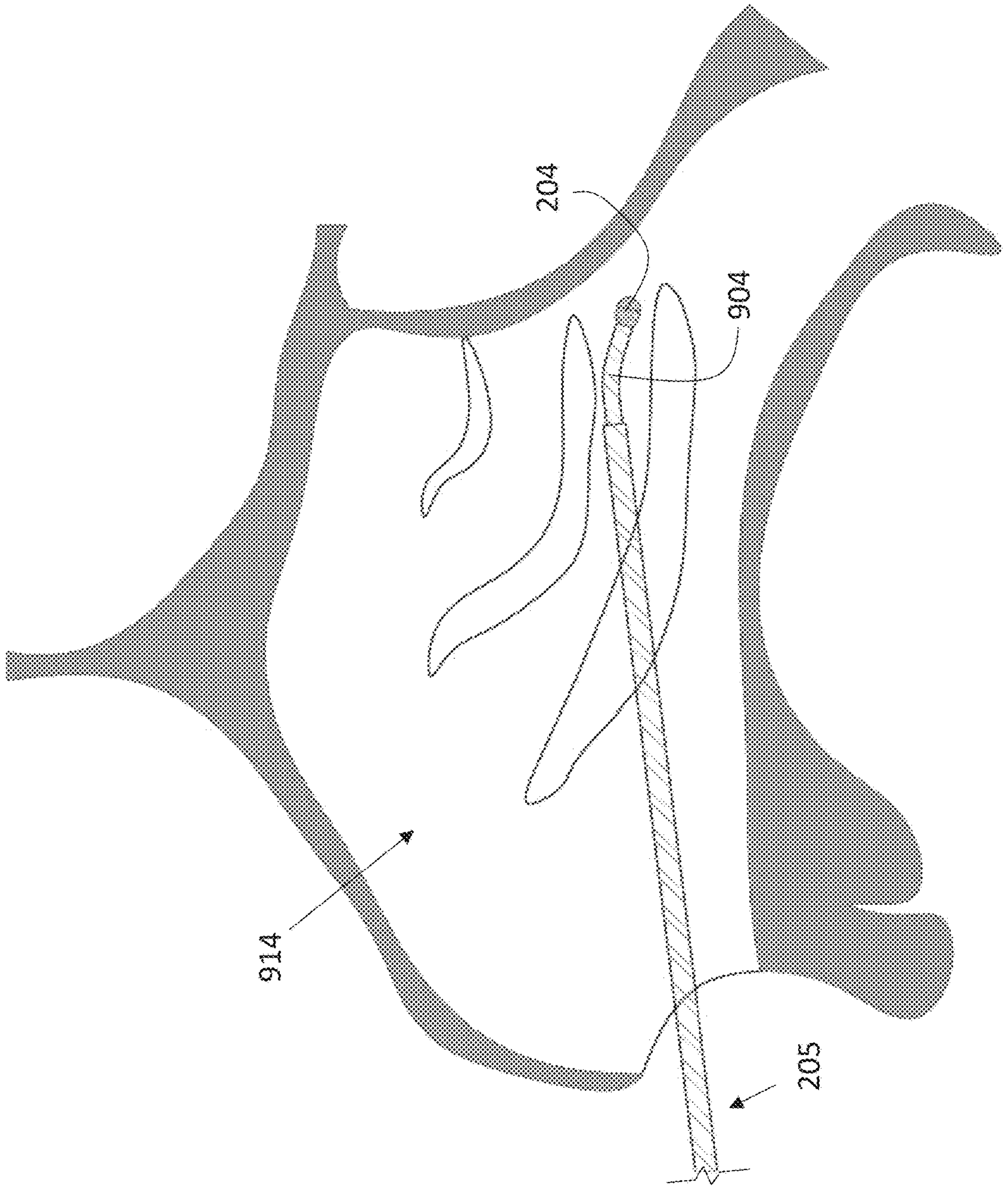
FIG. 11 shows a sectional view of a nasal cavity having therein the PFE delivery instrument of the system of FIG. 1, in accordance with some embodiments.
Figure 12:
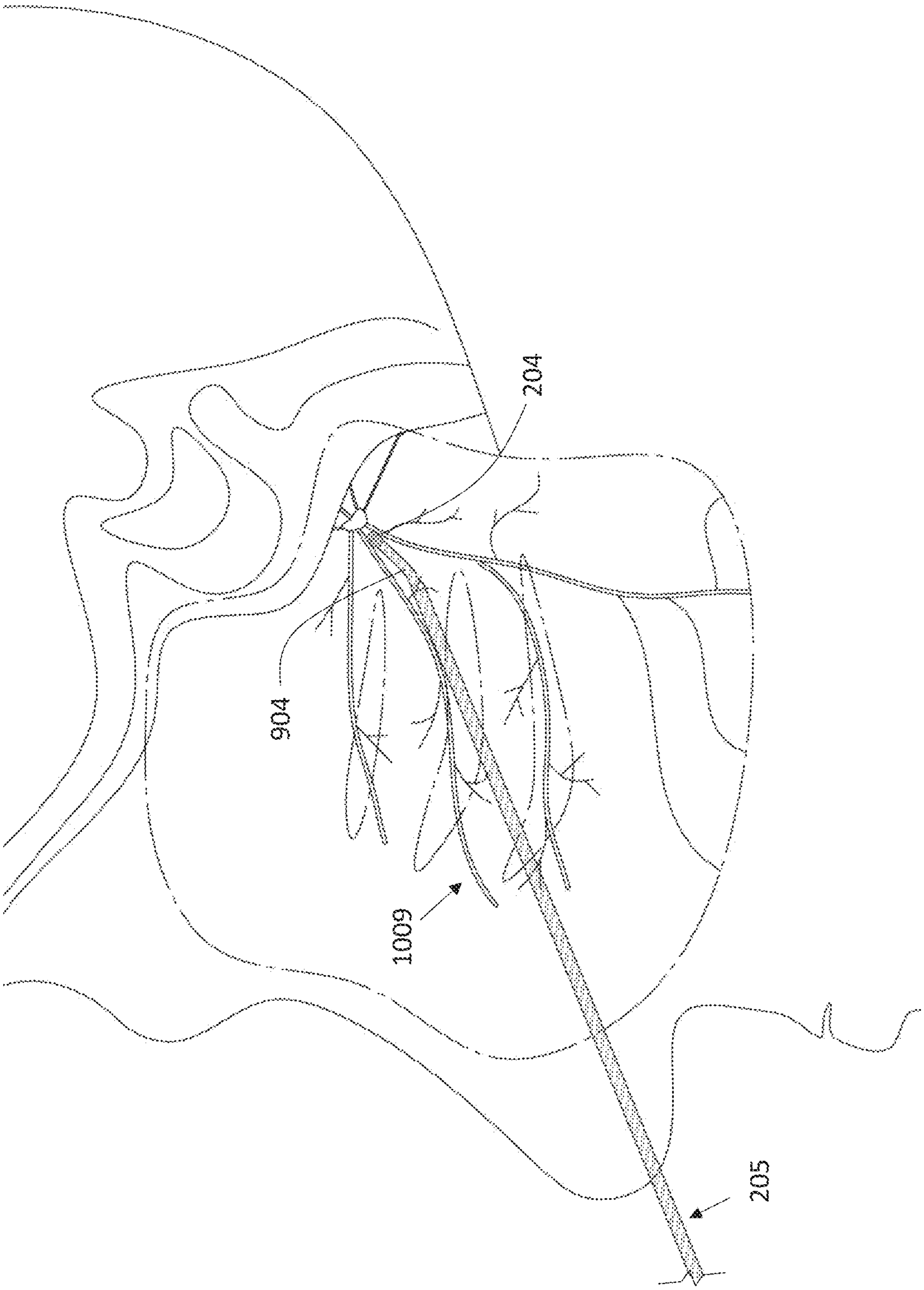
FIG. 12 shows a sectional view of a trigeminal nerve region having therein the PFE delivery instrument of the system of FIG. 1, in accordance with some embodiments.
Figure 13:
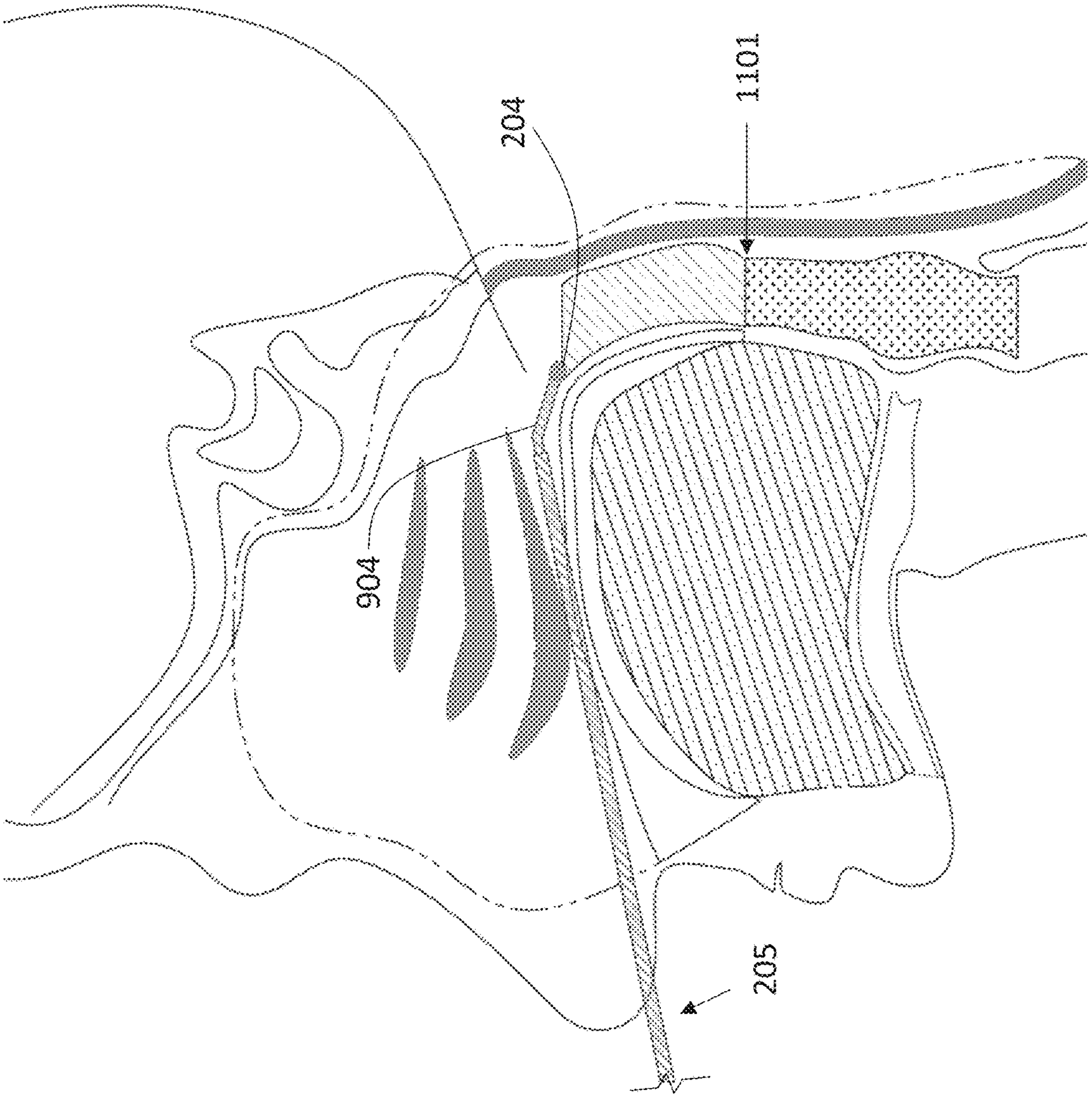
FIG. 13 shows a sectional view a throat having therein of the PFE delivery instrument of the system of FIG. 1, in accordance with some embodiments.

Referring now to FIGS. 11-13, some embodiments of system 10 can include the PFE delivery instrument 200 (FIGS. 1-3) that is sized and configured for ENT procedures to treat conditions such as chronic rhinitis, migraines, sleep apnea, snoring, and other conditions. In the depicted example, the elongated shaft 205 can include a distal tip 904 that can be bendable relative to elongated shaft 205. For example, as shown in FIG. 11, PFE delivery instrument 200 can be used within nasal cavity 914 to treat chronic rhinitis. PFE delivery instrument 200 can be advanced through nasal cavity 914 go targeted tissue. PFE delivery instrument 200 can deliver PFE pulses via an electrode at distal tip 214.

In the example depicted in FIG. 12, the distal tip 904 can be bent so a PFE electrode located at distal tip 904 is directed towards a posterior side of the inferior turbinate. Bending distal tip 904 can bring distal tip 904 closer to the inferior turbinate as compared with examples where distal tip 904 is not bent. Distal tip 204 of the instrument 200, once the generator 130 is activated, can deliver PFE treatment to the tissue to trigger the cellular apoptosis, thus replacing the faulty cells with healthy cells. In some embodiments, a region of the nasal cavity including faulty cells that can contribute to abnormal mucus secretion also include nerves 1009 which are involved in mucus secretion either due to neural degeneration, or environmental triggers that may include strong odors, cold air exposure, alcohol ingestion, and/or spicy foods. These signals generated by the neural network within the nasal cavity can result in chronic rhinitis (allergic or non-allergic), migraines, and/or other conditions. This means that, distal tip 204 can deliver PFE to both replace and regenerate cells through apoptosis and stimulate nerves 1009. In some examples, nerves 1009 can include the Sphenopalatine Ganglion (SPG). This can result in neural improvements and restoring of nerves to their normal functioning.

In the example depicted in FIG. 13, PFE delivery instrument 200 can treat a throat 1101 by inducing apoptosis in target tissue with PFE pulses (as described above in connection with FIGS. 1-4). Apoptosis can replace unhealthy cells with healthy cells, thus improving airflow during sleep for patients that have OSA. PFE delivery instrument can deliver PFE pulses via a PFE electrode at distal tip 204. The PFE pulses can both induce irreversible electroporation to destroy unhealthy cells through apoptosis and stimulate one or more nerves to restore normal nerve function. Replacing unhealthy cells with healthy cells and improving the neural functionality by stimulating the nerves within the throat 1101 ensure that the upper respiratory passage remains open during sleep and does not obstruct the airflow. This type of treatment can improve a breathing of patients who suffer from nasal valve collapse. During nasal valve collapse, the nasal valve or other anatomy within the upper respiratory system can collapse due to rapid breathing through the nose.

Accordingly, as described above in connection with FIGS. 1-5 and by further example uses depicted in FIGS. 11-13, it should be understood from the description herein that the PFE control console 100 and PFE delivery instrument 200 can be used in a variety of ENT procedures so as to deliver PFE therapy for the stimulation of any one of, or combination of, the Sphenopalatine Ganglion (SPG), posterior nasal nerves, the vidian nerve, and the optic nerve, all branches of the trigeminal nerve, other nerves within an ear nose or throat. Such nerve stimulation provided by the PFE system 10 detailed above can treat migraines, rhinitis, and other conditions by restoring the normal nerve activity by removing nerve stressors triggered from signals attributed to smells, allergic and non-allergic rhinitis, chronic rhinitis, or other nerve injuries.

Also as described in detail above, it should be understood from the description herein that the PFE control console 100 and PFE delivery instrument 200 can deliver PFE pulses 301 having high voltages (e.g., greater than 1,000 volts). This can ensure that PFE pulses 301 stimulate nerves below the mucosa that are responsible for triggering migraines, trigeminal neuralgia, and other forms of pain. The high amplitude of PFE pulses 301 can ensure that the pulses result in long lasting nerve restoration, thus reducing or eliminating a need for repeated neurostimulation. When treating certain conditions such as the soft palate for obstructive sleep apnea (OSA), PFE delivery instrument 200 can include a basket electrode 642 (refer to FIGS. 6-7) that compresses tissue and holds the tissue in place while PFE delivery instrument 200 delivers the PFE. By holding the tissue in place, basket electrode 642 can result in a more effective delivery of the PFE pulses to the adjacent tissue. Delivering PFE while mechanically compressing a soft palate with basket electrode 642 can significantly improve an outcome of the procedure. For example, by compressing the tissue, basket electrode 642 can ensure that it is in contact with all parts of the tissue that can benefit from treatment. Basket electrode 642 can deliver PFE pulses 301 so that healthy cell restoration occurs uniformly throughout tissue.

Additionally, as described above in connection with FIGS. 1-5 and by further example uses depicted in FIGS. 11-13, it should be understood from the description herein that the PFE control console 100 and PFE delivery instrument 200 can deliver PFE pulses 301 that improve a safety profile of the patient. For example, PFE pulses 301 can restore healthy tissue via apoptosis by killing unhealthy cells and preserving an extracellular matrix. Healthy cells can regrow within this extracellular matrix. For example, PFE delivery instrument 200 can deliver PFE treatment the middle ear plexus, trigeminal nerve, sphenopalatine ganglion, Eustachian tube (ET), and others locations, Since PFE delivery instrument 200 can deliver PFE in a way that does not cause damage to healthy ligaments, tissue, nerves, and other anatomical structures located within regions treated by PFE delivery instrument 200, PFE delivery instrument 200 avoid unintended injuries that can arise form systems that use RF treatment or ablation. PFE delivery instrument 200 can also treat soft tissue with little to no damage to critical structures such as nerves and blood vessels, even when these critical structures are located within the region of PFE delivery.

Optionally, as described above in connection with FIGS. 1-5 and by further example uses depicted in FIGS. 11-13, it should be understood from the description herein that the PFE control console 100 and PFE delivery instrument 200 can deliver PFE pulses 301 to treat asthma. Asthma affects the lungs by causing repeated episodes of wheezing, shortness of breath and coughing. One way to control asthma is to avoid triggers that may cause bronchospasm. PFE delivery instrument 200 can treat asthma by delivering PFE pulses to stimulate nerves in the upper and lower respiratory system, including nerves located in the nasal cavity, pharynx, larynx, trachea, and lungs. Application of pulsed field electroporation throughout the respiratory system, or within certain regions, can result in making the anatomical regions of application less susceptible to allergens or other irritants in the respiratory system, thus reducing or eliminating asthma episodes.

Within the upper respiratory airway, PFE delivery instrument 200 can treat tissue that might obstruct airflow in the respiratory system, such as the inferior turbinate, polyps, and tissue that might obstruct normal airflow. For example, PFE delivery instrument 200 can induce a tissue shrinkage process. This tissue shrinkage process occurs as PFE delivery instrument 200 induces irreversible electroporation in unhealthy cells that causes unhealthy cells to eventually die. When the cells regenerate, a volume of the cells can be smaller than a volume of the cells prior to being treated with PFE. This means that PFE delivery instrument 200 can enlarge an airway of patient 30 by delivering PVE to replace unhealthy cells with healthy cells. PFE delivery instrument 200 can open a space that was previously closed by diseased tissue, allowing airflow to move through the airways of the patient.

Referring now to FIGS. 14A-14F, in some embodiments, a display screen of the PFE control console 100 (FIG. 1, or optionally the display screen of the endoscope system 80 which is connected to the console 100 in FIG. 1) can display image data indicating a calculated PFE field size relative to the distal tip 204 of PFE delivery instrument 200. In some cases, endoscope instrument 50 can collect this image data displayed by control console 100. In use, in some embodiments, endoscope instrument 50 and PFE delivery instrument 200 can advance to a targeted site. Endoscope instrument 50 can capture a location of PFE delivery instrument 200 relative to anatomy of patient 30 at the targeted site. Medical images 1402-1404 each indicate distal tip 204 and a respective PFE field corresponding to distal tip 204. In this embodiment, the PFE control console 100 is configured to calculate an estimated size of a PFE field output from the PFE electrode (described below) and to overlay the calculated PFE field is a graphic upon the medical image of distal tip 204 on the display screen of user interface device 110 (FIG. 1, or optionally on the display screen of the endoscope system 80 which is connected to the console 100 in FIG. 1). The control console 100 can overlay the graphic of the calculated PFE field that is scaled to the proper size relative to the distal tip 204 and the anatomical features depicted in the medical images 1402-1404. For example, the graphic of the calculated PFE field can be overlaid on the electrode of distal tip 204 according to the proper size/scale shown in the medical images 1402-1404 so as to rapidly communicate to the user the actual physical locations of the PFE therapy relative to distal tip 204 shown on the display screen of user interface device 110.

Figures 14A, 14B, 14C, 14D, 14E, 14F:
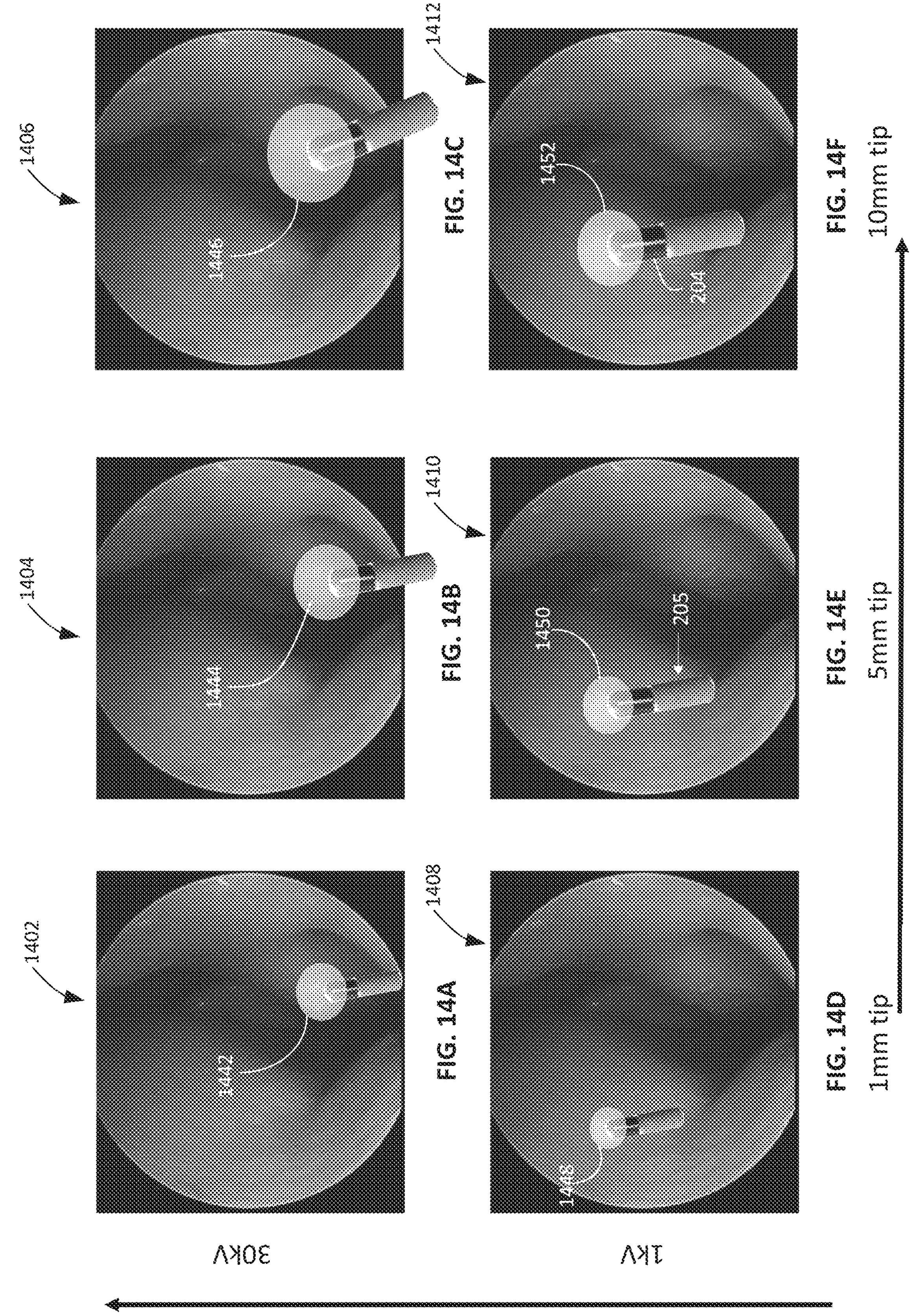
FIG. 14A-14F show endoscopic medical images of the instrument of the system of FIG. 1 including a visual representation of projected PFE fields, in accordance with some embodiments.

For example, in FIG. 14A, the graphic of the calculated PFE field 1442 output by distal tip 204 is sized based on the calculated size of the field (described below) and the size of the distal tip 204 of the instrument, thereby displaying where the PFE field reaches as a graphic of the semi-transparent white bubble graphic overlaid on distal tip 204. Similarly, in FIG. 14B, the graphic of the calculated PFE field 1444 output by distal tip 204 reaches points covered by the white bubble overlaid on distal tip 204, and so on. FIG. 14A illustrates an image 1402 of distal tip 204 and the graphic of the calculated PFE field 1442, where distal tip 204 includes a 1-mm tip electrode configured to output a 10 kilovolt (kV) PFE signal. FIG. 14B illustrates an image 1404 of distal tip 204 and the graphic of the calculated PFE field 1444, where distal tip 204 includes a 5-mm tip electrode configured to output a 10 kV PFE signal. FIG. 14C illustrates an image 1406 of distal tip 204 and the graphic of the calculated PFE field 1446, where distal tip 204 includes a 10-mm tip electrode configured to output a 10 kV PFE signal. FIG. 14D illustrates an image 1408 of distal tip 204 and the graphic of the calculated PFE field 1448, where distal tip 204 includes a 1-mm tip electrode configured to output a 1 kV PFE signal. FIG. 14E illustrates an image 1410 of distal tip 204 and the graphic of the calculated PFE field 1450, where distal tip 204 includes a 5-mm tip electrode configured to output a 1 kV PFE signal. FIG. 14F illustrates an image 1412 of distal tip 204 and the graphic of the calculated PFE field 1452, where distal tip 204 includes a 10-mm tip electrode configured to output a 1 kV PFE signal.

Figure 15:
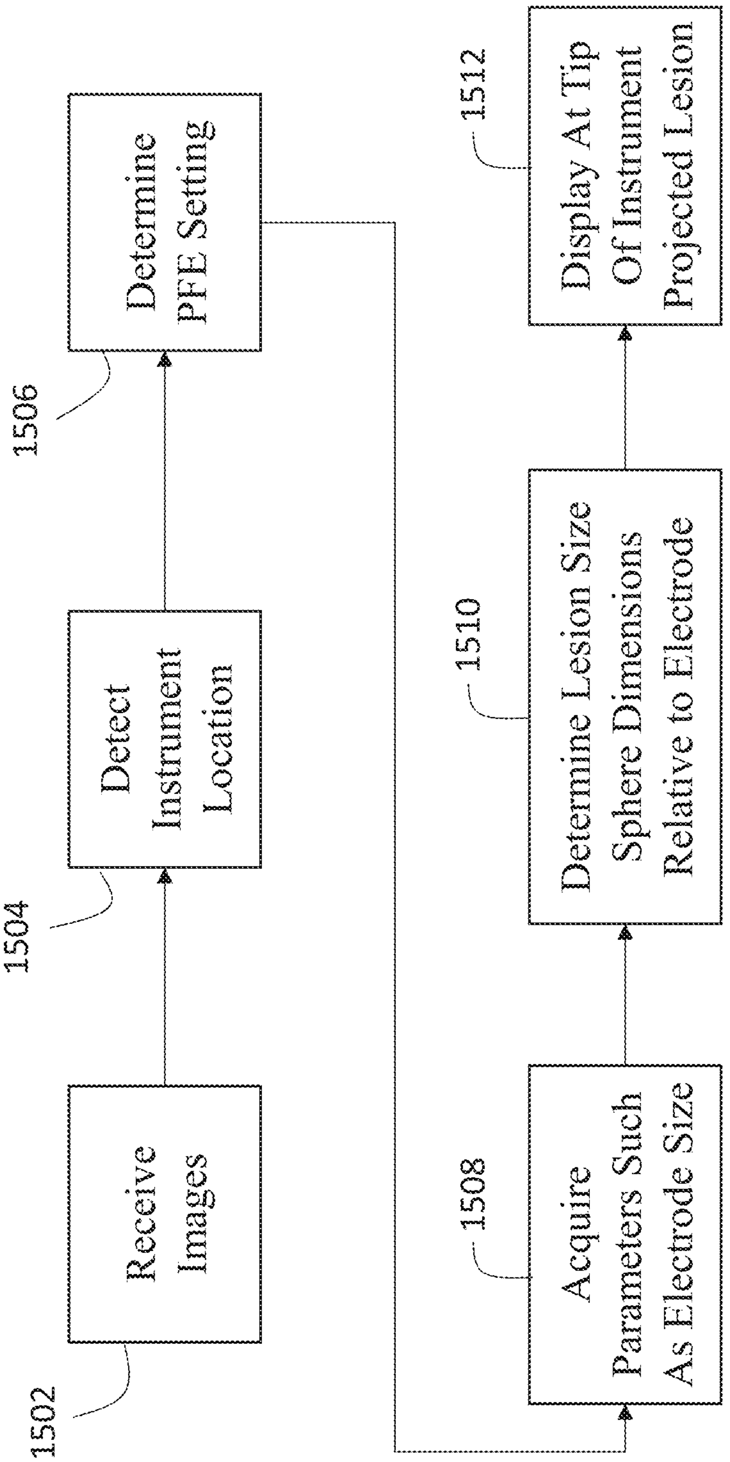
FIG. 15 is a flow diagram of an example method for generating a PFE field corresponding to PFE delivery instrument and overlaying the PFE field on image data.

Referring now to FIG. 15, some implementations of a computer-implemented method (e.g., executed by the PFE control console 100) can accurately generate a graphic of a calculated PFE field corresponding to PFE delivery instrument 200 and overlay the graphic of the calculated the PFE field on endoscopic image data. In some embodiments, control module 1502 is configured to receive, from endoscope instrument 50, endoscope image data depicting at least a distal tip 204 of the PFE delivery instrument 200 and one or more anatomical features of patient 30 (1502). In some examples, PFE delivery instrument 200 and endoscope instrument 50 are both inserted into an area within the car, nose, or throat of patient 30. The endoscope can advance so that a distal tip 204 of PFE delivery instrument 200 is within a field of view of endoscope instrument 50. This allows endoscope instrument 50 to capture distal tip 204 relative to one or more anatomical features of patient 30. User interface device 110 can display the endoscope data in real time.

The PFE control console 100 is configured to detect, based on the endoscope image data, a location of PFE delivery instrument 200 relative to anatomy of the patient 30 (1504). In some embodiments, this involves determining whether PFE delivery instrument 200 is proximate a targeted tissue site. Control console 100 can optionally apply a machine learning model to detect the location of PFE delivery instrument 200 relative to anatomy of the patient 30. Since user 20 can move endoscope instrument 50 and PFE delivery instrument 200 independently of each other, the lens of endoscope instrument 50 can move relative to distal tip 204. When endoscope instrument 50 is further away from distal tip 204, distal tip 204 appears smaller on the display screen of user interface device 110 and when endoscope instrument 50 is closer to distal tip 204, distal tip 204 appears larger on the display screen of user interface device 110. A machine learning model can process endoscope image data to determine a location of distal tip 204 relative to anatomy, accounting for a distance between distal tip 204 and the lens of endoscope instrument 50.

For example, the machine learning model can be trained using training data comprising a plurality of training images. Each of these training images can be associated with a distance between to objects in the image and a distance between an image capture device and the objects in the image. The machine learning model can be trained to recognize patterns that allow the machine learning model to determine, based on the endoscope image data, a location of the distal tip 204 relative to one or more anatomical features when a distance between the endoscope lens and the distal tip 204 is unknown. In some examples, the machine learning model can estimate a depth of the distal tip 204 within the endoscope image data. One kind of machine learning model that can estimate depth is a convolutional neural network (CNN).

Still referring to FIG. 15, the PFE control console 100 can determine one or more PFE settings corresponding to PFE delivered by PFE delivery instrument 200 (1506). These PFE settings can include, for example, any one or combination of PFE pulse amplitude, PFE pulse duration, PFE pulse frequency within pulse bursts, a number of PFE pulses within each pulse bursts, and a frequency at which pulse bursts are delivered. Control console 100 can acquire one or more physical parameters of PFE delivery instrument 200 such as a size of a PFE electrode on distal tip 204 (1508). Based on the detected location of PFE delivery instrument 200, the determined PFE settings, and the acquired physical parameters, control console 100 can determine a size of a PFE field (1510). For example, the control console 100 can determine a size and dimension of a space in which PFE pulses can reach relative to a location of the PFE electrode on distal tip 204.

In some examples of this computer-implemented method depicted in FIG. 15, to determine a size of the PFE field that will appear on the display screen of user interface device 110 (e.g., for the graphic of the calculated PFE field as shown in FIGS. 14A-14F), the PFE control console 100 can apply a machine learning model to estimate a depth of the distal tip 204 in the endoscope image data. The depth can indicate how large the PFE field appears on the display screen. For example, the PFE field will appear larger on a screen when the endoscope lens is closer to distal tip 204 and will appear smaller on the display screen when the endoscope lens is further away from the distal tip 204. Control console 100 can display the PFE field on the display screen of user interface device 110 in real time so that the PFE field is overlaid on an electrode at distal tip 204 (1512).

Figure 16A:
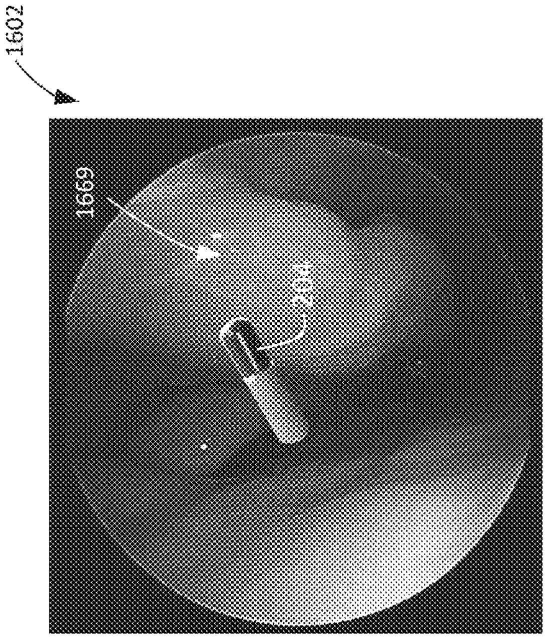
FIG. 16A-16D show endoscopic medical images of the instrument of the system of FIG. 1 relative to an anatomical landmark, in accordance with some embodiments.
Figure 16B:
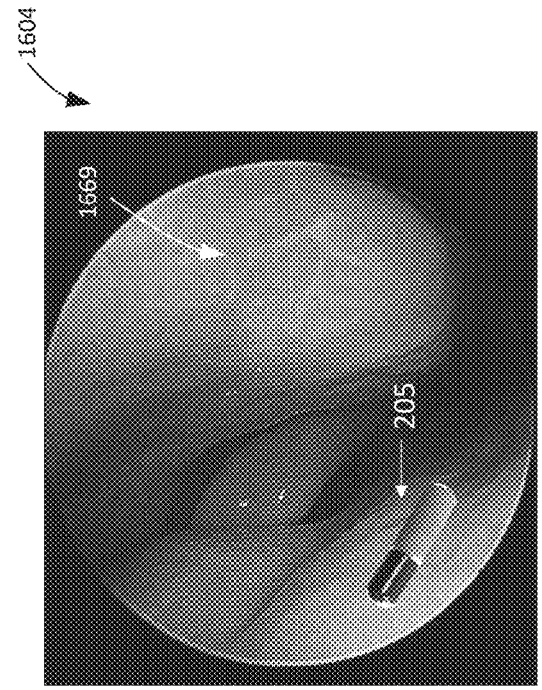
Figure 16C:
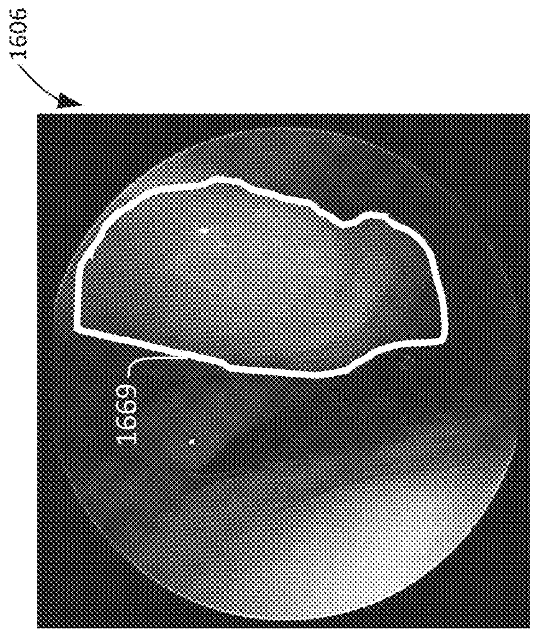
Figure 16D:
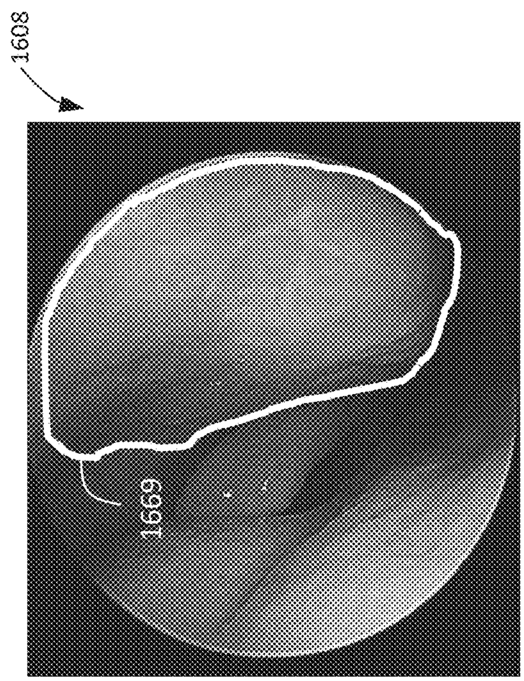

Referring now to FIGS. 16A-16D, the endoscope image data displayed by the user interface device 110 of the PFE control console (FIG. 1) can indicate a location of distal tip 204 of PFE delivery instrument 200 relative to a computer-identified anatomical landmark 1669 (e.g., such as inferior turbinate in this embodiment). Optionally, as described in more detail below (FIG. 17), the PFE control console can be equipped with enhanced safety to prevent the output of PFE pulses when the distal tip 204 is not located in proximity to particular (approved) anatomical region. Turning to the example images in FIGS. 16A-16D, the image 1602 in FIG. 16A shows the distal tip 204 relative to anatomical landmark 1669 in a first position. FIG. 16B illustrates an image 1604 of distal tip 204 relative to anatomical landmark 1669 in a second position. FIG. 16C illustrates an image 1606 of anatomical landmark 1669 in the first position outlined in white. FIG. 16D illustrates an image 1608 of anatomical landmark 1669 in the second position outlined in white. In some cases, control console 100 includes a machine learning model configured to recognize distal tip 204 and identify anatomical landmark 1669. The machine learning model can, in some embodiments, distinguish anatomical landmark 1669 from other anatomical landmarks. The machine learning model can determine a distance between distal tip 204 and anatomical landmark 1669. Examples of anatomical landmarks include the inferior turbinate, the septum, the throat, and the posterior nasal nerve. By determining in real time the identity of anatomical landmarks and a location of distal tip 204 relative to those landmarks, control console 100 can determine whether to deliver PFE via PFE delivery instrument 200.

Figure 17:
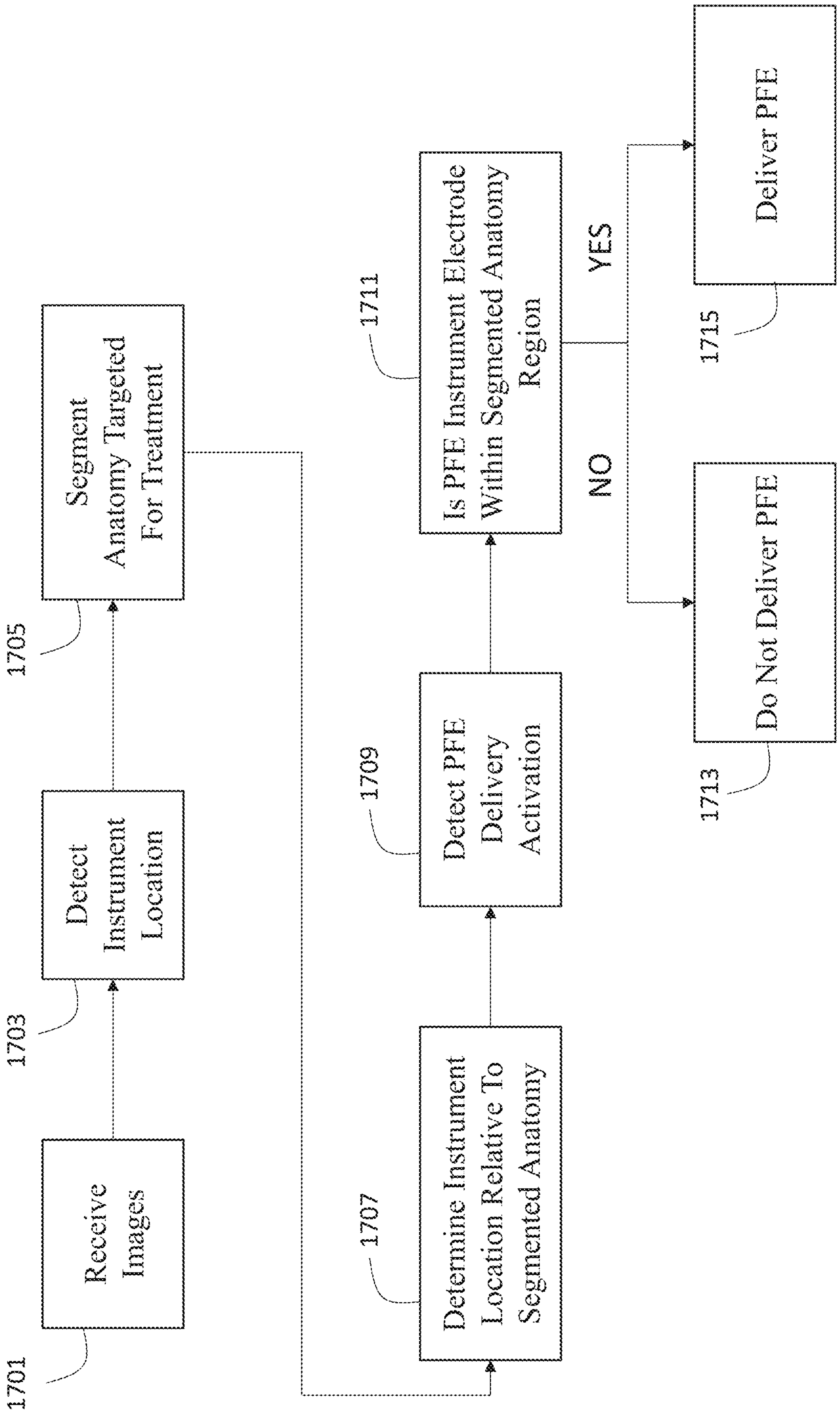
FIG. 17 is a flow diagram of an example method for processing endoscope image data to automatically determine whether to initiate output of PFE using a PFE delivery instrument.

Referring now to FIG. 17, some implementations of a computer-implemented method (e.g., executed by the PFE control console 100) can process endoscope data during an ENT procedure to automatically determine whether to output PFE using a PFE delivery instrument 200. For example, the PFE control console 100 implement the method to achieve enhanced safety that prevents the output of PFE pulses when the distal tip 204 is not located in proximity to particular (approved) anatomical region. For example, as shown in operation 1701, the PFE control console 100 can receive endoscope image data collected by endoscope instrument 50 in real time. This endoscope data can indicate a distal tip 204 and one or more anatomical features of patient 30. Also, in operation 1703, the PFE control console 100 can apply a machine learning model do detect a location of distal tip 204 relative to the one or more anatomical features. This operation can include determining a depth of the distal tip 204 relative to the one or more anatomical features relative to the endoscope lens.

In operation 1705, the PFE control console 100 can segment anatomy targeted for treatment using PFE delivery instrument 200. Preferably, control console 100 uses a machine learning model to segment the anatomy. Machine learning models can segment images by assigning a label or category to each pixel in the image, effectively dividing the image into regions corresponding to different objects or classes. For example, targeted anatomy can be within one segment of the image, and that segment can be split into sub-segments.

In some cases, to train a machine learning model to segment endoscope image data, control console 100 can collect a dataset of image frames of endoscope image data where each image frame is annotated with pixel-level labels. These labels can indicate an object or class to which each pixel belongs (e.g., PFE delivery tool, inferior turbinate). This is called labeled training data. Control console 100 can train the machine learning model using labeled training data to recognize patterns corresponding to the labels which the trained machine learning model can apply to segment image data that is not labeled. CNNs are one kind of machine learning model that is beneficial for segmenting image data. In some embodiments, the machine learning model is trained using by applying a loss function to the labeled training data that penalizes discrepancies between the predicted segmentation and the ground truth annotations. For example, the machine learning model predicts a segmentation based on labeled frames and learns to minimize a difference between the predicted segmentation and the labels, which are the ground truth. During training, the machine learning model can learn to identify features in the images that are relevant for segmentation and to make accurate predictions. The trained machine learning model can therefore accurately identify objects such as distal tip 204 and one or more anatomical features in endoscope data captured in real time and displayed on the user interface device 110.

Still referring to FIG. 17, in operation 1707, the PFE control console 100 can determine a location of distal tip 204 of PFE delivery instrument 200 relative to segmented anatomy. This can involve determining a depth of delivery instrument 200 and the segmented anatomy to determine a distance between the delivery instrument 200 and the segmented anatomy. Machine learning models such as CNNs can be used to estimate a depth of objects within an image. In operation 1709, the PFE control console 100 can detect that PFE delivery is activated. In operation 1711, Based on PFE delivery being activated, control console 100 can determine whether PFE delivery instrument 200 is within a segmented anatomy region for delivering the PFE. As shown at operation 1713, based on the PFE delivery instrument 200 not being within the segmented anatomy region for delivering the PFE ("NO" at block 1711), control console 100 prevent the output PFE pulses using PFE delivery instrument 200 (even if the user actives the footswitch 70 in FIG. 1). As shown at operation 1715, based on the PFE delivery instrument 200 being within the segmented anatomy region for delivering the PFE ("YES" at block 1711), control console 100 can active the output of PFE pulses using PFE delivery instrument 200 (for example, because the machine learning model accurately identified that the distal tip 204 is located within a safe range of the segmented anatomy region.

Figure 18:
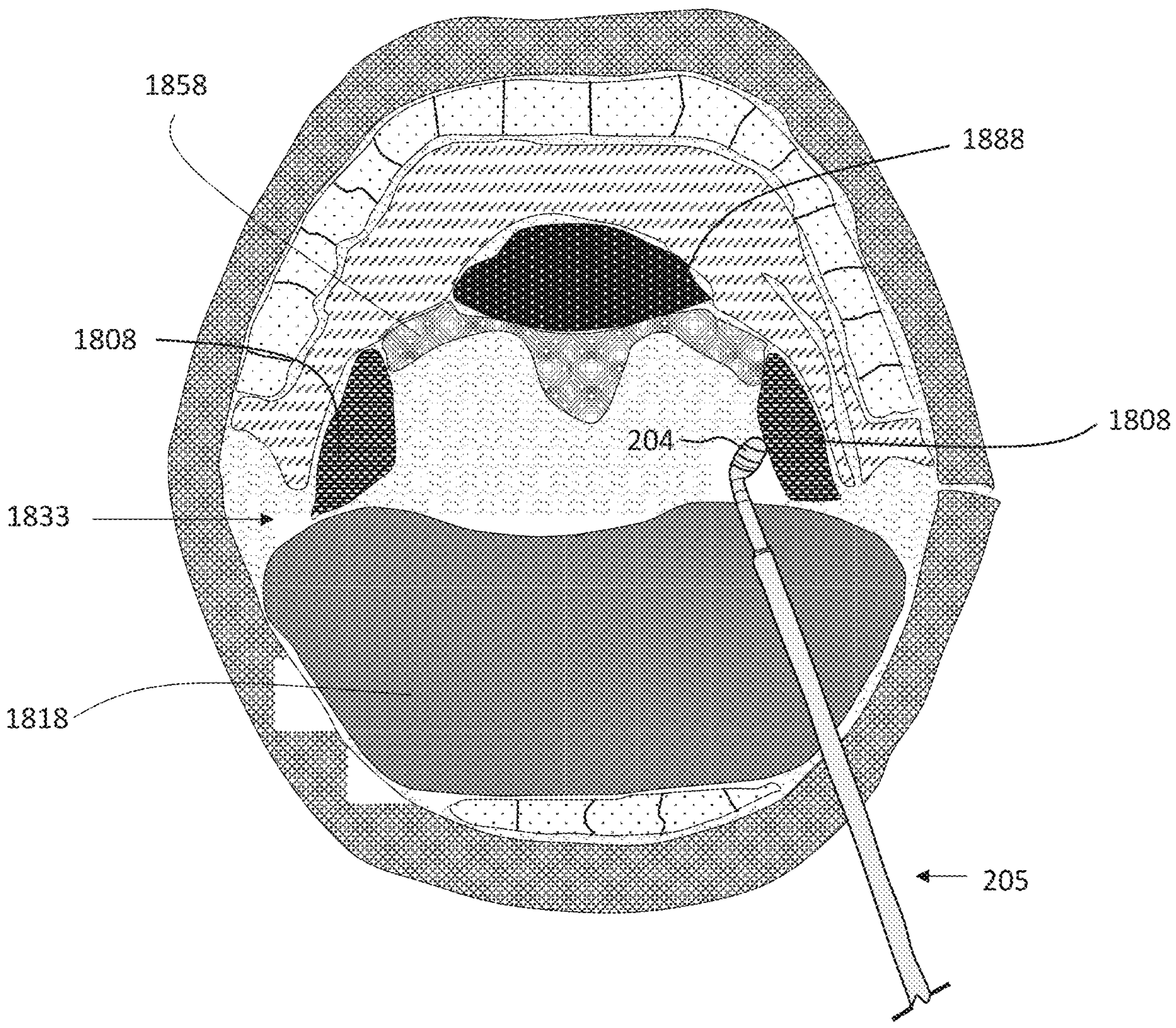
FIG. 18 shows a section view of a tonsils and adenoids region having therein the FE delivery instrument of the system of FIG. 1, in accordance with some embodiments.

Referring now to FIG. 18, some embodiments of system 10 include using the PFE delivery instrument 200 including elongated shaft 205 and distal tip 204 (as described in FIGS. 1-5) to treat tonsils 1808 and adenoids 1888. For example, instrument 200 can be advanced to the tonsils 1808 or adenoids 1888. When distal tip 204 is proximate to targeted tissue at the tonsils 1808 or adenoids 1888, PFE delivery instrument 200 can deliver PFE to treat the targeted tissue. System 10 is not limited to using PFE delivery tool illustrated in FIG. 17 to treat tonsils 1808 and adenoids 1888. Other delivery tools can be used, such as a delivery tool including a basket electrode (e.g., basket electrode 642) or a stent (e.g., stent electrode 815). PFE delivery instrument 200 can treat areas within oral cavity 1833 such as the tongue 1818, tonsils 1808, soft palate 1858, adenoids 1888, and other structures within the oral cavity. PFE delivery instrument 200 can sometimes treat malignant or benign cancer cells within the oral cavity 1833. PFE delivery instrument 200 can deliver PFE to targeted tissue to induce the apoptosis, triggering lymphocytes to rush to the targeted tissue and thus release T and B cell types that can fight cancerogenic tissue.

Figure 19:
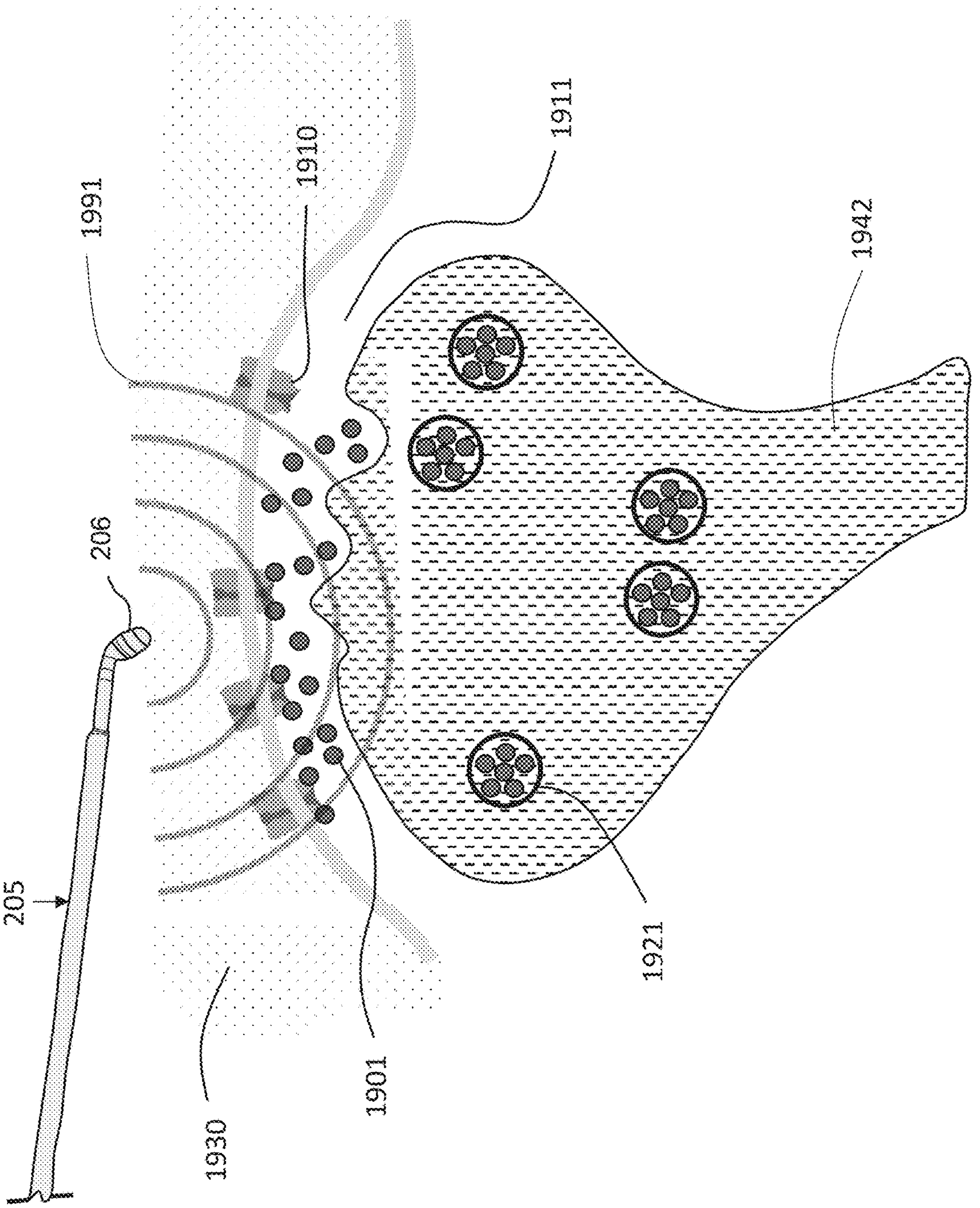
FIG. 19 shows a side view of an optional instrument of the system of FIG. 1 configured to stimulate a neuron.
Figure 20:
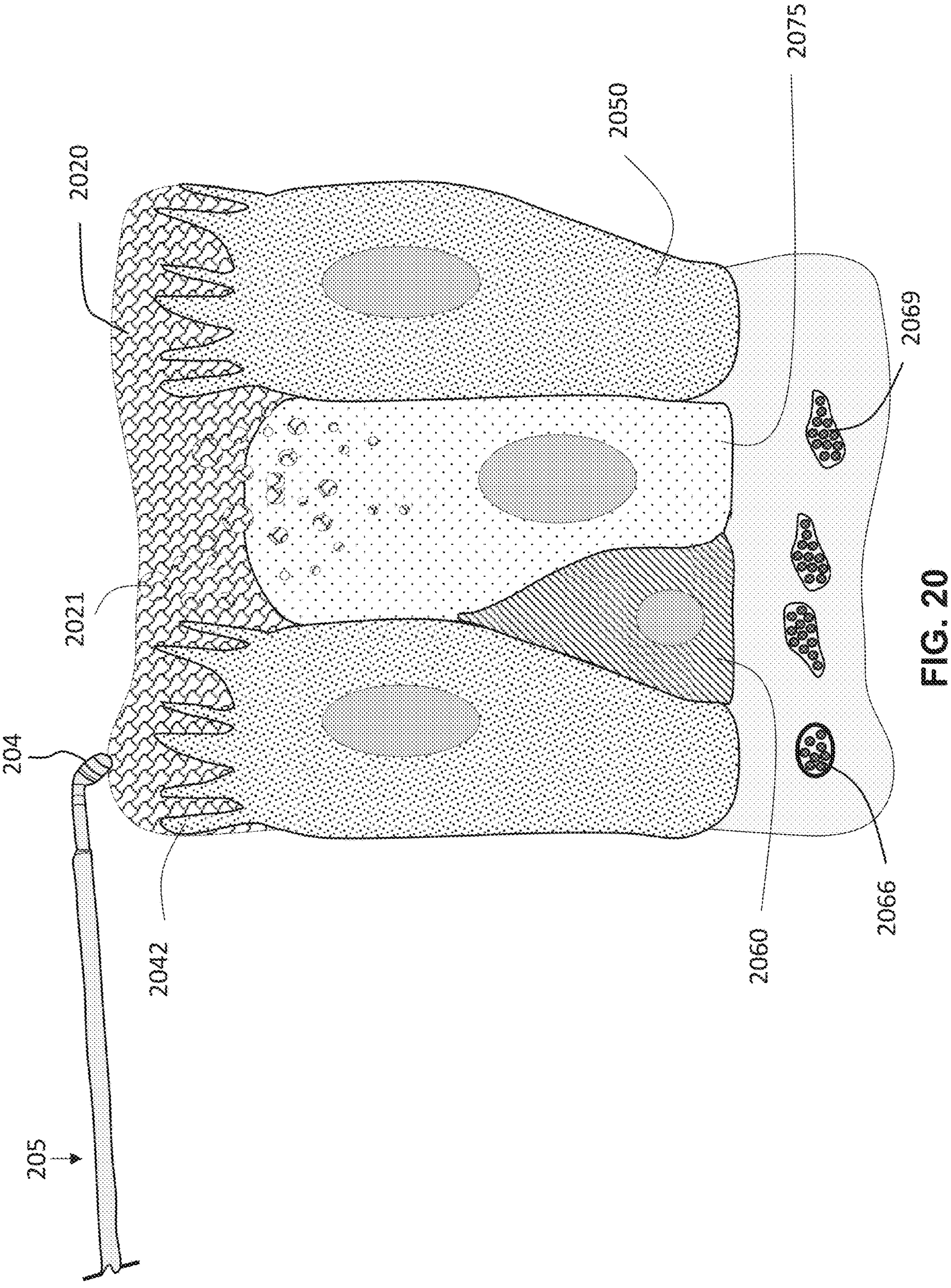
FIG. 20 shows a side view of an optional instrument of the system of FIG. 1 configured to treat a synapse of neurons of goblet cells.

Referring now to FIGS. 19-20, some embodiments of system 10 include using the PFE delivery instrument 200 (as described in FIGS. 1-5) to provide both apoptosis-inducing PFE pulses (for tissue treatment) and neurostimulation (for restoration of healthy neural functioning). For example, PFE delivery instrument 200 can stimulate neuron 1942, treat synapse junction 1911, restore vesicles 1921 to a healthy state, and trigger an apoptosis event on the cell body 1930 and the receptors 1910 as shown in FIG. 19. For example, the cell body 1930 including receptors 1910 can be a diseased cell, which disrupts a functioning of neuron 1942. By delivering PFE, PFE delivery instrument 200 can induce apoptosis in cell body 1930 so that the cell dies and is replaced with a healthy cell. The PFE can also restore normal functioning in nerve 1942 by restoring normal communication between nerve 1942 and receptors 1910. In some embodiments, PFE electrode 206 of PFE delivery instrument 200 can deliver an irreversible electroporation field 1991.

For example, PFE delivery instrument 200 can stimulate bundle 2066 of goblet cell 2075 so that mucus glands 2069 and/or goblet cell 2075 depletes mucus located deep into the tissue 2021, or within the tissue 2020. This ensures that the tissue is totally or partially cleared from excessive mucus. This can also ensure that the tissue is totally or partially cleared form mucus trapped within the tissue. PFE can also restore the vesicles 1921 so that they do not produce excessive mucus 2020 by erratically signaling to goblet cells 2075 to produce mucus. This can be achieved using PFE to stimulate the nerve 1942 so that vesicles 1921 are overworked to the point that the channels have depleted neurotransmitters 1901. In some embodiments, vesicles 1921, the synapse junction 1911, and the cell body 1930 do not communicate with each other due to the synapse 1911 being cleared from neurotransmitters 1901, PFE delivered by PFE delivery instrument 200 can seal vesicles 1921 and receptors 1910.

Some embodiments of system 10 include using the PFE delivery instrument 200 to stimulate the neuron 1942, treat synapse junction 1911, restore vesicles 1921 to healthy state, and trigger an apoptotic event on the cell body 1930 and the receptors 1910 as shown in FIG. 19. Furthermore, PFE delivery instrument 200, as shown in FIG. 20, can deliver PFE to induce apoptosis on the cells that consist of cilia 2050 thus terminating them from converting into mucus producing goblet cells 2075.

PFE delivery instrument 200 can induce electroporation in cell body 1930, neurotransmitters 1901, vesicles 1921, and synapse junction 1911 such that the cell body 1930 dies through apoptosis. PFE delivery instrument 200 can restore the neurotransmitters 1901 and synapse junction 1911 to a normal state by removing and replacing neurotransmitters 1901 over time. PFE delivery instrument 200 can restore vesicles 1921 may to release neurotransmitters 1901 so that synapse junction 1911 carries a signal traveling from the nerve 1942 to the cell receptors 1910.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A pulsed field electroporation (PFE) system configured to deliver PFE pulses to nasal tissue, comprising:

a handheld PFE tool having a handle, an elongated shaft extending distally from the handle toward a bendable distal shaft portion, and a bulbous treatment tip extending distally from the bendable distal shaft portion and having a PFE electrode configured to deliver PFE pulses to nasal tissue adjacent to the bulbous treatment tip, the bulbous treatment tip having a maximum lateral width of less than 5 mm and being insertable into a nasal passageway; and a PFE control console configured to receive a connector of the handheld PFE tool, the PFE control console including a user interface display and a PFE generator configured to output from the PFE electrode a pulsed field according to a predefined pattern of pulses having a voltage within a range from 850 V to 10,000 V and a pulse duration of 0.05 microseconds (µs) to 3 µs to induce irreversible electroporation in the nasal tissue, wherein the predefined pattern of pulses comprises a sequence of bursts of electrical pulses, wherein each burst of electrical pulses comprises a high-frequency pulse train, wherein the bursts of electrical pulses occur at a first frequency, and wherein the electrical pulses of each high-frequency pulse train occur at a second frequency lower than the first frequency.

2. The PFE system of claim 1, wherein the PFE generator is configured to output from the PFE electrode the pulsed field to induce apoptosis in the nasal tissue without changing a targeted tissue treatment temperature more than 5 degree C.

3. The PFE system of claim 2, wherein the PFE control console is connectable to an endoscope system to receive medical image data from the endoscope system such that endoscopic images of the treatment tip of the handheld PFE tool are displayed at the user interface display of the PFE control console.

4. The PFE system of claim 3, wherein the bulbous treatment tip has a rigid shape with a single PFE electrode exposed along an exterior of the bulbous treatment tip, the maximum lateral width of the bulbous treatment tip being 2 mm to 4 mm.

5. The PFE system of claim 1, wherein the PFE control console is connectable to a return electrode pad configured to adhere to a skin of a patient, and wherein the PFE generator is configured to output the pulsed field from the PFE electrode to induce irreversible electroporation in the nasal tissue of the patient so that the pulsed field returns to the PFE control console via the return electrode pad on the skin of the patient.

6. The PFE system of claim 5, wherein the PFE control console is connectable to a footswitch, and wherein the PFE control console is configured to activate the PFE generator for outputting the pulsed field in response to receiving a user input via the footswitch.

7. The PFE system of claim 1, wherein the first frequency is within a range from 500 kilohertz (kHz) to 10,000 kHz, and wherein the second frequency is within a range from 1 hertz (Hz) to 100 Hz.

8. The PFE system of claim 1, wherein a separation gap occurs between each pair of consecutive bursts of electrical pulses of the sequence of bursts of electrical pulses, and wherein a separation gap occurs between each pair of consecutive electrical pulses of the high-frequency pulse train that is shorter than the separation gap that occurs between each pair of consecutive bursts of electrical pulses of the sequence of bursts of electrical pulses.

9. The PFE system of claim 8, wherein a duration of the separation gap that occurs between each pair of consecutive bursts of electrical pulses of the sequence of bursts of electrical pulses is within a range from 0.005 seconds to 1 second, and wherein a duration of the separation gap that occurs between each pair of consecutive electrical pulses of the high-frequency pulse train is within a range from 0.05 us to 3 µs.

10. The PFE system of claim 8, wherein each high-frequency pulse train is configured to induce the irreversible electroporation in the nasal tissue, and wherein the separation gap that occurs between each pair of consecutive bursts of electrical pulses of the sequence of bursts of electrical pulses prevents the handheld PFE tool from delivering thermal ablative energy.

11. The PFE system of claim 10, wherein the separation gap between each burst of electrical pulses of the sequence of bursts of electrical pulses allow the handheld PFE tool to stimulate one or more nerves by delivering the sequence of bursts of electrical pulses.

12. The PFE system of claim 11, wherein the high-frequency pulse train of each burst of electrical pulses of the sequence of bursts of electrical pulses includes a number of electrical pulses within a range from 10 electrical pulses to 500 electrical pulses.

13. The PFE system of claim 1, wherein each electrical pulse of the high-frequency pulse train comprises a monophasic waveform.

14. The PFE system of claim 1, wherein each electrical pulse of the high-frequency pulse train comprises a biphasic waveform.

15. The PFE system of claim 1, wherein the electrical pulses of the high-frequency pulse train alternate between having a positive amplitude and having a negative amplitude.

16. The PFE system of claim 1, wherein the pulsed field comprises a sequence of bursts of electrical pulses, and wherein each burst of electrical pulses of the sequence of bursts of electrical pulses comprises a plurality of pulse groups.

17. The PFE system of claim 16, wherein each pulse group of the plurality of pulse groups comprises first pulse having a positive polarity followed by a second pulse having a negative polarity.

18. The PFE system of claim 16, wherein each pulse group of the plurality of pulse groups comprises first pulse having a positive polarity, followed by a second pulse having a negative polarity, followed by a third pulse having a positive polarity.

19. The PFE system of claim 16, wherein each pulse group of the plurality of pulse groups comprises first pulse having a negative polarity, followed by a second pulse having a positive polarity, followed by a third pulse having a negative polarity.

20. The PFE system of claim 1, wherein an angle of the bendable distal shaft portion is adjustable.

21. The PFE system of claim 20, wherein the angle of the bendable distal shaft portion is adjustable in response to pressure applied to the bendable distal shaft portion.

22. The PFE system of claim 20, wherein the handheld PFE tool includes an actuator on the handle, the actuator configured to receive a user input to adjust the angle of the bendable distal shaft portion during a procedure to deliver the PFE pulses to the nasal tissue.

23. The PFE system of claim 22, wherein the actuator is slidable relative to the handle along a longitudinal axis of the handle, and wherein the angle of the bendable distal shaft adjusts based on the actuator sliding relative along the longitudinal axis of the handle.

* * * * *